(12) United States Patent
Becq et al.

(10) Patent No.: US 6,630,482 B1
(45) Date of Patent: Oct. 7, 2003

(54) CFTR CHANNEL ACTIVATOR COMPOUNDS AND PHARMACEUTICAL COMPOSITIONS CONTAINING SAME

(75) Inventors: Frédéric Becq, Aix en Provence (FR); Yvette Mettey, Saint-Benoit (FR); Jean-Michel Vierfond, Maisons Alfort (FR); Bernard Verrier, Roquevaire (FR); Maurice Gola, Aubagne (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/230,747

(22) PCT Filed: Jul. 31, 1997

(86) PCT No.: PCT/FR97/01436

§ 371 (c)(1),
(2), (4) Date: Mar. 2, 1999

(87) PCT Pub. No.: WO98/05642

PCT Pub. Date: Feb. 12, 1998

(30) Foreign Application Priority Data

Aug. 1, 1996 (FR) .......................................... 96 09721

(51) Int. Cl.$^7$ .................. A61K 31/4375; C07D 455/06
(52) U.S. Cl. ........................ 514/294; 546/95; 546/71; 514/284
(58) Field of Search ................ 514/294, 284; 546/95, 71

(56) References Cited

U.S. PATENT DOCUMENTS

| | | | |
|---|---|---|---|
| 3,306,896 A | 2/1967 | Ely | 260/240 |
| 3,320,269 A | 5/1967 | De Wald | 260/296 |
| 3,462,446 A | 8/1969 | De Wald | 260/295 |
| 4,329,349 A | 5/1982 | Damon et al. | 424/256 |

FOREIGN PATENT DOCUMENTS

| | | |
|---|---|---|
| EP | 0 227 932 | 7/1987 |
| EP | 0 480 717 | 4/1992 |
| FR | 2 342 285 | 9/1977 |
| GB | 2 054 593 | 2/1981 |
| JP | 08 198875 | 8/1996 |
| WO | WO 94/03431 | 2/1994 |
| WO | WO 96/16084 | 5/1996 |

OTHER PUBLICATIONS

Vierfond, J–M. et al. : Synthesis of derivatives of benzo(c) quinolizine. J. heterocycl. Chem. vol. 16, pp. 753–755, 1979.*
Chemical Abstracts, vol. 125, No. 14, Sep. 1996, Abstract No. 182124.
Chemical Abstracts, vol. 125, No. 11, Sep. 1996, Abstract No. 142014.
Chemical Abstracts, vol. 124, No. 20, May 1996, Abstract No. 275034.
Chemical Abstracts, vol. 123, No. 21, Nov. 1995, Abstract No. 285267.
Chemical Abstracts, vol. 120, No. 17, Apr. 1994, Abstract No. 216578.
Chemical Abstracts, vol. 120, No. 17, Apr. 1994, Abstract No. 216577.
Chemical Abstracts, vol. 120, No. 9, Feb. 1994, Abstract No. 106684.
Chemical Abstracts, vol. 119, No. 7, Aug. 1993, Abstract No. 72812.
Chemical Abstracts, vol. 117, No. 11, Sep. 1992, Abstract No. 111563.
Chemical Abstracts, vol. 115, No. 1, Jul. 1991, Abstract No. 8539.
Chemical Abstracts, vol. 110 No. 15, Apr. 1989, Abstract No. 135039.
Chemical Abstracts, vol. 108 No. 19, May 1988, Abstract No. 167815.
Chemical Abstracts, vol. 107, No. 7, Aug. 1987, Abstract No. 58801.
Chemical Abstracts, vol. 106, No. 13, Mar. 1987, Abstract No. 102038.
Chemical Abstracts, vol. 106, No. 13, Mar. 1987, Abstract No. 102,037.
Chemical Abstracts, vol. 106, No. 7, Feb. 1987, Abstract No. 49539.
Chemical Abstracts, vol. 103, No. 1, Jul. 1985, Abstract No. 6194.
Chemical Abstracts, vol. 98, No. 11, Mar. 1983, Abstract No. 89325.
Chemical Abstracts, vol. 96, No. 21, May 1982, Abstract No. 180360.
Chemical Abstracts, vol. 95, No. 11, Sep. 1981, Abstract No. 97225.
Chemical Abstracts, vol. 95, No. 11, Sep. 1981, Abstract No. 97225.
Chemical Abstracts, vol. 93, No. 5, Aug. 1980, Abstract No. 46363.
Chemical Abstracts, vol. 92, No. 3, Jan. 1980, Abstract No. 22363.
Chemical Abstracts, vol. 90, No. 9, Feb. 1979, Abstract No. 72026.
Chemical Abstracts, vol. 89, No. 5, Jul. 1978, Abstract No. 43063.
Chemical Abstracts, vol. 83, No. 23, Dec. 1975, Abstract No. 193051.
Chemical Abstracts, vol. 82, No. 19, May 1975, Abstract No. 125239.
Chemical Abstracts, vol. 74, No. 5, Feb. 1971, Abstract No. 22658.

(List continued on next page.)

Primary Examiner—Charanjit S. Aulakh
(74) Attorney, Agent, or Firm—Young & Thompson

(57) ABSTRACT

CFTR channel activator compounds from the benzo[c] quinolizinium family or families of compounds derived therefrom, as well as pharmaceutical compositions containing said compounds, and the uses thereof, particularly for treating cystic fibrosis, are disclosed.

1 Claim, 12 Drawing Sheets

OTHER PUBLICATIONS

Figure 1A:
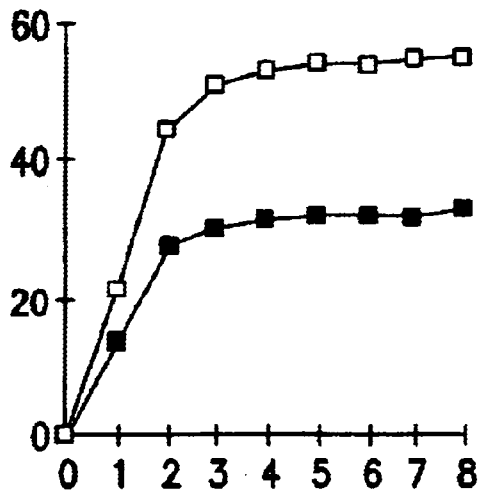

*Chemical Abstracts Service,* "Registry handbook 1977 Supplement", American Chemical Society.
*Chemical Abstracts Service,* "Registry handbook 1974 Supplement", American Chemical Society.
*Chemical Abstracts Service,* "Registry Handbook 1965–1971", America, Chemical Society.
by C.Paul Bianchi, "Pharmacology", *Chemical Abstracts,* vol. 110, No. 15, Apr. 1989, Abstract No. 135039.
by C. Paul Bianchi, "Pharmacology", *Chemical Abstracts,* vol. 106, No. 7, Feb. 1987, Abstract No. 49539.
By C. Paul Bianchi, "Pharmacodynamics", *Chemical Abstracts,* vol. 92, No. 3, Jan. 1980, Abstract No. 21823.
by C. Paul Bianchi, "Pharmacodynamics", *Chemical Abstracts,* vol. 91, No. 21, Nov. 1979, Abstract No. 175163.
by C. Paul Bianchi, "Pharmacodynamics", *Chemical Abstracts,* vol. 93, No. 5, Aug. 1980, Abstract No. 46363.
by C. Paul Bianchi, "Pharmacodynamics", *Chemical Abstract,* vol. 81, No. 11, Sep. 1974, Abstracts No. 63583.
by C. Paul Bianchi, "Pharmacology", *Chemical Abstracts,* vol. 120, No. 19, May 1994, Abstract No. 241028.
by A.R.E. Carey et al. "Keto–Enol and Imine–Enamine Tautomerism of 2–, 3– and 4–Phenacylpyridines", *Journal of the Chemical Society, Perkin Transactions 2,* vol. 11, 1993, pp. 2285–2296.
by T. Konakahara et al., "Stereoselective Synthesis of trans–2–Aryl–3– (2–pyridyl)aziridines from an α–Silyl Carbanion", *Journal of the Chemical Society, Perkin Transactions 1,* vol. 7, 1987, pp. 1489–1493.
by R.A.M. O'Ferrall et al., "$^1$H and $^{13}$C NMR Spectra of α–Heterocyclic Ketones and Assignment of Keto, Enol and Enaminone Tautomeric Structures", *Journal of the Chemical Society, Perkin Transactions 2,* vol. 19, 1994, pp. 2461–2470.
by F. Becq et al., "Phosphatase inhibitors activate normal and defective CFTR chloride channels", *Proc. Natl. Acad. Sci. USA,* vol. 91, Sep. 1994, pp. 9160–9164.

* cited by examiner

CFTR CHANNEL ACTIVATOR COMPOUNDS AND PHARMACEUTICAL COMPOSITIONS CONTAINING SAME

This application is a 371 of PCT/FR97/01436 filed Jul. 31, 1997, now WO 98/05642 Feb. 12, 1998.

The present invention relates to CFTR channel activator compounds, pharmaceutical compositions comprising the latter, and their use in the context of treatment of pathologies such as cystic fibrosis.

In an epithelial cell, transportation of water and electrolytes is associated with an increase in the permeability of the membranes to the ions $K^+$, $Na^+$ and $Cl^-$. These movements are linked to the activity of ion channels, that is to say specialized proteins integrated into the membrane allowing passive diffusion of ions. The techniques of molecular electrophysiology (patch clamping) allow recording at the unit level of the openings and closings of an ion channel and make it possible to study transepithelial ion transportations their regulation and their pathological dysregulation.

Among the numerous pathologies associated with the physiology of epithelial cells, cystic fibrosis is also regarded as a pathology of ion channels to the extent that the protein involved is a chloride channel, the CFTR channel, meaning "cystic fibrosis transmembrane conductance regulator". Mucoviscidosis, or cystic fibrosis (CF) in Anglo-Saxon terminology, is the most common recessive autosomal genetic disease in Caucasian populations. In the United States and in the majority of European countries, the incidence of carriers of the CF gene is 1 in 20 to 1 in 30. Cystic fibrosis affects the exocrine glands of the human organism. The main expression sites of the CFTR protein are the exocrine pancreas, the lungs, the sudoriparous glands, the intestine and the cardiac tissue. The attention paid to this disease has had significant consequences on understanding the secretory mechanisms of normal epithelial cells. The epithelial cells of the exocrine glands of the intestine, the pancreas or the lungs control transportation of salt and water into these organs. In cases of cystic fibrosis, mutations of the CF gene alter the properties and function of the CFTR channel. The transportation of electrolytes then becomes abnormal and leads to chronic pulmonary obstructive disorders, to pancreatic insufficiency, to bacterial pulmonary conditions, to an abnormally concentrated sudoriparous secretion and to masculine infertility. The defective secretion is linked with functioning of selective ion channels for chloride ions (CFTR channels) which are located in the apical membrane of cells and the activity of which is controlled by the cyclic AMP route.

The protein CFTR is a glycoprotein of 1.480 amino acids of molecular weight 170 kD divided into five fields (Riordan et al. 1989), two transmembrane segments each with 6 alpha-helices (numbered 1 to 12, each comprising 21 to 22 amino acids), two nucleotide binding fields (NBF1 and 2) and a large hydrophilic regulation field (field R). The protein CFTR, from its molecular structure, belongs to the family of membrane transporters (ABC meaning ATP-binding cassette).

The ABC transporters constitute a family of membrane proteins which are highly conserved in evolution. They are involved in the translocation of various substrates through cell membranes. However, while in prokaryotes several transporter/substrate pairs have been defined, this information is rarer in eukaryotes. In mammals, the majority of ABS transporters are associated with a pathology. The protein CFTR involved in cystic fibrosis, glycoprotein P (MDR: multi-drug resistance) involved in the rejection of antitumoral cytotoxic drugs and the protein ABC 1, recently described as playing an essential role in endocytosis of apoptotic bodies by the macrophage, may be mentioned. CFTR controls the transportation of transepithelial chloride and hydration of mucous compartments, while one of the isoforms of MDR is involved in the translocation of phosphatidylcholine. These three ABC proteins, which have a structure of two times 6 transmembrane segments, have two fields which bind and hydrolyse nucleotides (NBF) and a regulator field. The regulation of CFTR has been studied in particular.

Two complex processes control the activity of the CFTR channel: phosphorylation of field R by kinase proteins and binding (and perhaps hydrolysis) of ATP on the two NBF fields. The dephosphorylation of the CFTR channel causes a loss in activity of the channel up to its closure (Tabcharani et al., 1991, Becq et al. 1993a. Becq et al., 1994). In addition, the CFTR channel is associated with a membrane phosphatase which controls the activity and state of phosphorylation of the channel (Becq et al., 1993b. Becq et al., 1994).

The gene which codes for the protein CFTR has been isolated by molecular cloning and identified on chromosome 7 (Kerem et al., 1989, Riordan et al., 1989). The identification of the gene and its involvement in cystic fibrosis has been confirmed by the location of a deletion of three base pairs in a coding region (exon 10) of the CF gene originating from CF patients. This mutation corresponds to the deletion of a phenylalanine in position 508 ($\Delta$F508) of the protein in NBF1. The frequency of occurrence of this mutation is 70% on average in the gene analyses (Tsui & Buchwald. 1991). The consequences of this mutation are dramatic, since the abnormal protein produced by transcription of the mutated gene ($\Delta$F508) is no longer capable of ensuring its function in the transportation of chloride of the epithelial cells affected. The absence of a chlorine current after stimulation of epithelial cells of exocrine glands by cAMP is the main characteristic demonstrating the presence of an anomaly of the CF gene, and in particular the mutation ($\Delta$F508). More than 300 mutations have been identified to date on the CF gene. The highest density of mutations is found in the two nucleotide binding fields. The mutation ($\Delta$F508) is found in 70% of cases, and 50% of patients are homozygous for this mutation. Seven other significant mutations are present with incidences of greater than 1%. The mutation G551D corresponds to replacement of a glycine residue (G) in position 551 of the protein by an aspartic acid (D). Patients who carry this mutant have a severe pathology with a pancreatic insufficiency and serious pulmonary disorders (Cutting et al., 1990). The incidence of observation of this mutation reaches 3 to 5% in certain CF populations. In contrast to the $\Delta$F508 deletion, the protein CFTR carrying the mutation G551D is mature and is incorporated into the membrane (Gregor et al., 1991). However, the mutation causes an impermeability of the membrane and stimulation of the cAMP route does not open the channel associated with expression of this mutant (Gregory, et al., 1991. Becq et al., 1994).

Other mutations, such as R117H, R334W and R347P, appear with low incidences of 0.8, 0.4 and 0.5% respectively, and are associated with a less serious pathology (Sheppard et al., 1993). Expression of these three mutants generates a mature glycosylated form of the protein in harmony with its insertion into the membrane.

However, the three mutants are capable of responding to stimulation of the AMP route by opening of the channels. The amplitude of the currents, the unit conductance and the probability of opening of the channel associated with each of the three mutants are modified with respect to the normal CFTR channel (Sheppard et al., 1993. Becq et al., 1994). However, regulation by kinases/phosphatases seems normal for these various mutants, including the mutants G551D and ΔF508 (Becq et al., 1994).

These observations thus show that it is possible pharmacologically to activate a large number of CFTR mutants, including G551D and ΔF508. In spite a lack of directing of the protein ΔF508 in the membranes of epithelial cells affected by cystic fibrosis, several teams have shown that this protein could be present in a functional manner in the membranes (Dalemans et al., 1991, Drumm et al., 1991. Becq et al., 1994). It therefore seems necessary and of primary importance to develop a strategy for opening CFTR channels to optimize the chances of success of a treatment, but also to replace gene treatment EN,here this is not necessary (mutations other than ΔF508).

In spite of the progress made in the genetics of cvstic fibrosis and the biology and biochemistry of the protein CFTR, the pharmacology of openers of the CFTR channel is not very ell developed. Three families of molecules are currently put forward for their properties as activators or openers of the CFTR channel: phenylimidazothiazoles (levamisole and bromotetramisole), benzimidazolones (NS004) and xanthines (IBMX, theophylline . . . ).

1) The phenylimidazothiazoles (levamisole and bromotetramisole)

It has recently been shown that levamisole and bromotetramisole, by inhibiting a membrane phosphatase, allow control of the activity and the level of phosphorylation of the CFTR channel (Becq et al., 1994). These compounds open the CFTR channel in a dose-dependent manner (Becq et al., 1996) and act on the CFTR channel with mutations at the source of the disease (Becq et al., 1994). The mode of action of these activators is still uncertain. These molecules do not act by the conventional routes of cAMP or of intracellular calcium. Compounds of the bromotetramisole family already have a therapeutic use (Grem, 1990), and levamisole is used in certain lung treatments (Van Eygen et al., 1976, Dils. 1979). The latter properties represent a certain advantage for initiating clinical trials. However, these molecules do not, seem able to act in all cells. Intestinal cells respond poorly and opening of the CFTR after expression in the Xenopus ovocyte cannot be initiated. Furthermore, in a transgenic mouse model with the mutation G551D/G551D. bromotetramisole does not have the activator effect expected. The effects of these molecules therefore seem limited.

2) The benzimidazolones (NS004)

Gribkoff et al., 1994 recently demonstrated that NS004, a compound (benzimidazolone) derived from the imidazole nucleus, like levamisole, can open the channel under certain conditions (if the CFTR has been phosphorylated). However, benzimidazolones are also activators of numerous potassium channels (Olesen et al., 1994) and as a result are not very specific for CFTR.

3) The xanthines (IBMX, theophylline . . . ).

The xanthines, such as IBMX (3-isobutyl-1-methylxanthine) are CFTR activators. The action mechanism is still poorly known and several possibilities exist. By inhibiting intracellular phosphodiesterases (degradation enzymes of cAMP), xanthines can increase the level of cAMP and therefore activate CFTR. Other possibilities are currently being put forward, such as binding of xanthines on the nucleotide binding fields (NBF) of CFTR.

The object of the present invention is to provide CFTR channel activator compounds which are more specific for CFTR than the CFTR channel activator compounds described to date.

In this respect, the object of the present invention is to provide new medicaments for treatment of pathologies associated with disorders in transmembrane ion flow, in particular of chlorine, in the epithelial cells of a human or animal organism.

The object of the present invention is more particularly to provide new medicaments which can be used in the context of treatment of cvstic fibrosis, of prevention of rejection of cytotoxic drugs (in particular antitumoral drugs), or of prevention or treatment of obstructions of bronchial routes or of digestive tracts (in particular pancreatic or intestinal), or also in the context of treatment of cardiovascular diseases.

Another object of the present invention is to provide a preparation process for the compounds and pharmaceutical compositions of the invention.

A subject of the present invention is the use of compounds of general formula (I) Which follows:

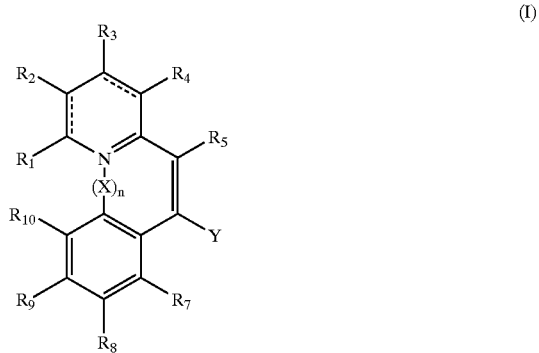

(I)

in which:
heterocycle A is aromatic or non-aromatic, it being understood that in the latter case the nitrogen atom of this heterocycle is linked by a double bond to the carbon in position 4a.

$R_1$, $R_2$, $R_3$, $R_4$, R5, $R_7$, R8, $R_9$ and $R_{10}$, represent, independently of each other:
a hydrogen, or bromine or fluorine atom, or
a halogen atom, in particular a chlorine atom, or
an alkyl, alkoxy, carbonyl or oxycarbonyl group, linear or branched, with approximately 1 to approximately 10 carbon atoms, these groups being substituted if appropriate, in particular by a halogen, and/or by a hydroxyl, and/or by an amine (primary, secondary or tertiary), and/or by an aromatic and/or aliphatic cycle, with approximately 5 to approximately 10 carbon atoms in the cycle, these cycles being themselves, if appropriate, substituted in particular by a halogen, and/or by a hydroxyl, and/or by an amine (primary, secondary or tertiary), and/or by an alkyl. alkoxy, carbonyl or oxycarbonyl group, these groups being as defined above, or
an aromatic or aliphatic cycle, with approximately 5 to approximately 10 carbon atoms in the cycle, these cycles being itself, if appropriate, substituted in particular by a halogen, and/or by a hydroxyl, and/or by an amine (primary, secondary or tertiary), and/or by an alkyl, alkoxy, carbonyl or oxycarbonyl group, these groups being as defined above, or an $OR_a$ group, $R_a$ representing a hydrogen atom or an alkyl, carbonyl or oxycarbonyl group, linear or branched, these groups being as defined above, or an aromatic or aliphatic cycle, these cycles being as defined above, or an $NR_bR_c$ group, $R_b$ and $R_c$ independently of each other representing an alkyl, alkoxy, carbonyl or oxycarbonyl group, linear or branched, these groups being as defined above, or an aromatic or aliphatic cycle, these cycles being as defined above, or when $R_1$ and $R_2$, or $R_3$ and $R_4$, and/or $R_4$ and $R_5$, and/or $R_7$ and $R_8$, and/or $R_8$ and $R_9$, and/or $R_9$ and $R_{10}$, do not represent the different atoms or groups or cycles mentioned above, then $R_1$ in combination with $R_2$, or $R_2$ in combination with $R_3$, and/or $R_3$ in combination with $R_4$, and/or $R_4$ in combination with $R_5$, and/or $R_7$ in combination with $R_8$, and/or $R_8$ in combination with $R_9$, and/or $R_9$ in combination with $R_{10}$, form respectively with $C_1$ and $C_2$, or with $C_2$ and $C_3$, or with $C_3$ and $C_4$ or with $C_4$, $C_{4a}$ and $C_5$ or with $C_7$ and $C_8$ or with $C_8$ and $C_9$ or with $C_9$ and $C_{10}$, an aromatic or aliphatic cycle, with 5 to 10 carbon atoms, if appropriate this cycle being substituted. in particular by a halogen, and/or by an alkyl, alkoxy, carbonyl or oxycarbonyl group and/or an aromatic or aliphatic cycle, these groups or cycles being as defined above, or when $R_3$ and $R_4$ do not represent the different atoms or groups or cycles mentioned above, then $R_3$ in combination with $R_4$ form an indole group of formula

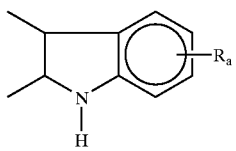

in which $R_a$ is as defined above,

Y represents:
an $OR_4$ group. $R_d$ representing a hydrogen atom or an alkyl, carbonyl or oxycarbonyl group, linear or branched, these groups being as defined above, or an aromatic or aliphatic cycle, these cycles being as defined above, or an $NR_eR_f$ group, $R_e$ and $R_f$ independently of each other, representing an alkyl, alkoxy, carbonyl or oxycarbonyl group, linear or branched, these groups being as defined above, or an aromatic or aliphatic cycle, these cycles being as defined above, it being understood that when $R_d$, or at least one of $R_e$ and $R_f$ do not represent one of the different atoms or groups or cycles mentioned above, then $R_d$, or at least one of $R_e$ and $R_f$, in combination with $R_5$, or in combination with $R_7$, form respectively with $C_5$ or $C_6$, or with $C_6$, $C_{6a}$ and $C_7$, an aromatic or aliphatic heterocycle with 5 to 10 carbon atoms, if appropriate substituted, in particular by a halogen, and/or an alkyl, alkoxy, carbonyl or oxycarbonyl group, and/or an aromatic or aliphatic cycle, these groups or cycles being as defined above, n is equal to 0 or 1, with:
when n is equal to 0:
X represents an atom in anionic form, such as a halogen atom, in particular a bromine or chlorine atom, or a group of atoms in anionic form, such as a perchlorate, and the nitrogen of heterocycle A of formula (I) is in quaternary form and is linked on the one hand by covalent bond to the carbon in position 11, and, on the other hand, by ionic bond to X defined above, it being understood that when $R_1$ and $R_{10}$ do not represent the different atoms or groups or cycles mentioned above, then $R_1$ in combination with $R_{10}$ form with $C_1$, the nitrogen of heterocycle A of formula (I), $C_{11}$, and $C_{10}$, an aromatic or aliphatic heterocycle with 5 to 10 carbon atoms, if appropriate substituted, by a halogen, and/or an alkyl, carbonyl or oxycarbonyl group, and/or by an aromatic or aliphatic cycle, these groups or cycles being as defined above, when n is equal to 1, then X represents a hydrogen atom, or a halogen atom, in particular a bromine, or chlorine, or fluorine atom.

For the preparation of medicaments intended for the treatment of pathologies in particular pulmonary, digestive or cardiac, linked to transmembrane ion flow disorders, in particular chlorine and, if appropriate, bicarbonate, in the organism (human or animal), in particular for the preparation of medicaments intended for the treatment of mucoviscidosis, or for the prevention of rejection of cytotoxic drugs (in particular antitumoral), for the treatment of obstructions to the bronchial routes or digestive tracts (in particular pancreatic or intestinal).

A more particular subject of the invention is the use as described above, of compounds of general formula (I) in which n=1, and corresponding to the derivatives of general formula (11) which follow:

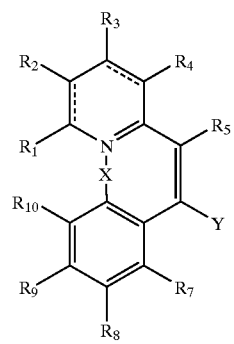

(II)

in which $R_1$, $R_2$, $R_3$, $R_4$, $R_5$, $R_7$, $R_8$, $R_9$, $R_{10}$, X and Y are as defined above.

Therefore, the invention also more particularly relates to the use as described above, of the compounds of general formula (IIa) which follows:

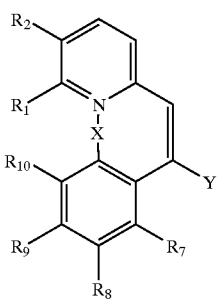
(IIa)

in which

R$_1$ and R$_2$ represent a hydrogen atom, or form in combination with C$_1$ and C$_2$ an aromatic cycle with 6 carbon atoms, Y represents an —OH or NH$_2$ group, R$_7$, R$_8$, R$_9$ and R$_{10}$ represent a hydrogen atom, or one of R$_7$, R$_8$, R$_9$ or R$_{10}$, represents a halogen atom, in particular a bromine, chlorine or fluorine atom, X represents a hydrogen atom or a halogen atom, in particular a bromine, chlorine or fluorine atom.

The compounds of general formula (IIa) advantageously used within the scope of the present invention, are those chosen from the following:

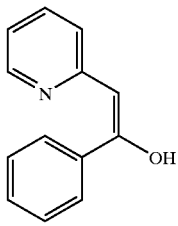
(compound 1)

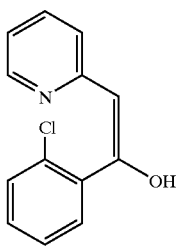
(compound 2)

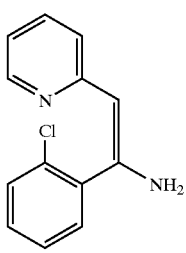
(compound 3)

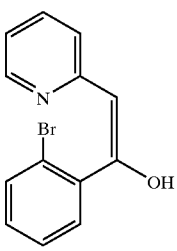
(compound 4)

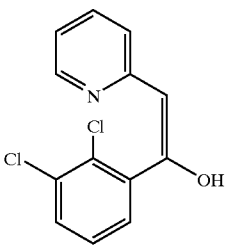
(compound 5)

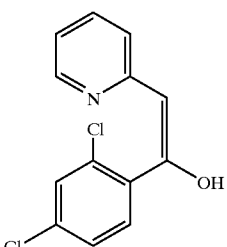
(compound 6)

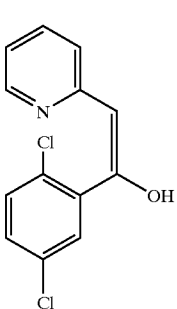
(compound 7)

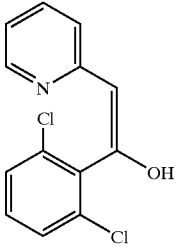
(compound 8)

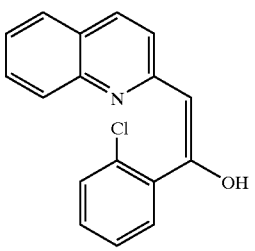
(compound 9)

-continued (compound 10)

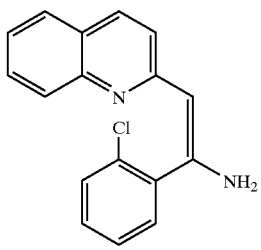

More particularly the invention also relates to the use as described above, of compounds of general formula (IIb) which follows:

(IIb)

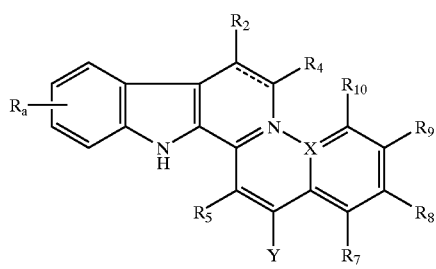

in which $R_3$, $R_1$, $R_2$, $R_5$, $R_7$, $R_8$, $R_9$, $R_{10}$, X and Y are as defined above, and in particular the compounds of formula (IIb) in which:

$R_a$ represents a hydrogen atom, $R_1$ and $R_2$ represent a hydrogen atom, and there is no double bond between the two carbons carrying $R_1$ and $R_2$, $R_5$ represents a hydrogen atom, $R_7$, $R_8$, $R_9$, and $R_{10}$ represent a hydrogen atom, or one of $R_7$, $R_8$, $R_9$, and $R_{10}$ represents a halogen atom, in particular a chlorine, bromine or fluorine atom, Y represents —$NH_2$, X represents a halogen atom, in particular a bromine, chlorine or fluorine atom.

The compounds of formula (IIb) advantageously used within the scope of the present invention, are those chosen from the following:

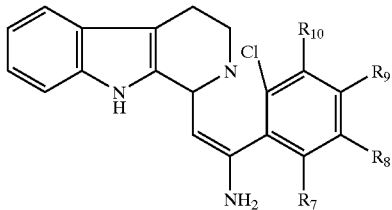

compound A: $R_7$=Cl, $R_8$=$R_9$=$R_{10}$=H,
compound B: $R_7$=$R_8$=$R_9$=$R_{10}$=H,
compound C: $R_8$=Cl, $R_7$=$R_9$=$R_{10}$=H,
compound D: $R_9$=Cl, $R_7$=$R_8$=$R_{10}$=H,
compound E: $R_{10}$=Cl, $R_7$=$R_8$=$R_9$=H,
compound F: $R_9$=Br, $R_7$=$R_8$=$R_{10}$=H.

A more particular subject of the invention is the use as described above, for the compounds of general formula (I) in which n=0, and corresponding to benzo[c]quinolizinium derivatives of formula (III) which follows:

(III)

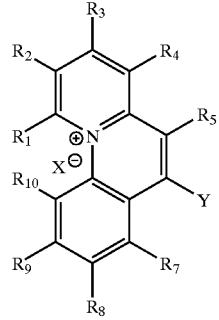

in which $R_1$, $R_2$, $R_3$, $R_4$, $R_5$, $R_7$, $R_8$, $R_9$, $R_{10}$, X and Y are as defined above.

Therefore, the invention more particularly relates to the use as described above, of the compounds of general formula (IIIa) which follows:

(IIIa)

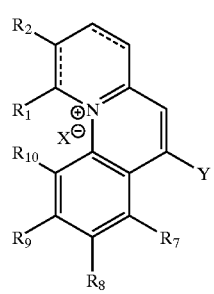

in which:

$R_1$ and $R_2$ represent a hydrogen atom, or form in combination with $C_1$ and $C_2$ an aromatic cycle with 6 carbon atoms, Y represents an —OH or —$NH_2$ or $NHCOCH_3$ group, $R_7$, $R_8$, $R_9$ and $R_{10}$, represent a hydrogen atom or one of $R_7$, $R_8$, $R_9$ and $R_{10}$ represents a halogen atom, in particular a chlorine, bromine or fluorine atom, X represents a halogen atom in anionic form, in particular a bromine atom $Br^-$, or a chlorine atom $Cl^-$, or a group of atoms in anionic form, in particular a perchlorate $ClO_4^-$.

Particularly preferred compounds within the scope of the present invention are those of formula (IIIa) in which:

$R_1$ and $R_2$ represent a hydrogen atom,

Y represents an —OH group,

X represents a halogen atom in anionic form, in particular a bromine atom $Br^-$, or a chlorine atom $Cl^-$, or a group of atoms in anionic form, in particular a perchlorate $ClO_4^-$, $R_7$, $R_8$, $R_9$ and $R_{10}$, represent independently of each other a hydrogen atom or a halogen atom, in particular a chlorine, bromine or fluorine atom.

Compounds of general formula (IIIa) advantageously used within the scope of the present invention are those chosen from the following:

(compound 11 or MPB-26)
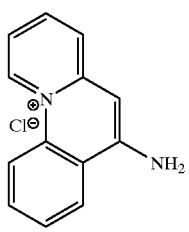
(compound 12 or MPB-05)
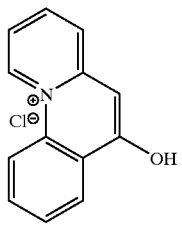
(compound 13 or MPB-01)
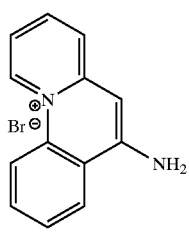
(compound 14 or MPB-02)
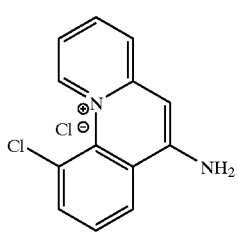
(compound 15 or MPB-03)
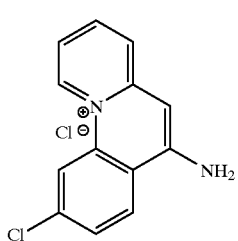
(compound 16)
(compound 17)
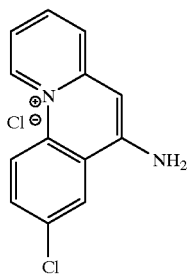
(compound 18 or MPB-06)
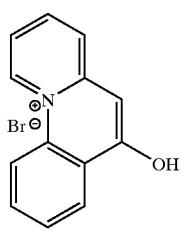
(compound 19 or MPB-07)
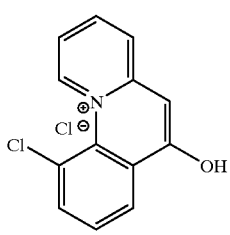
(compound 20 or MPB-08)
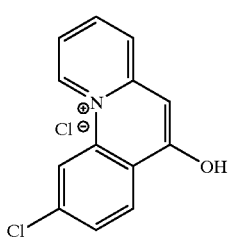
(compound 21 or MPB-27)
(compound 22)
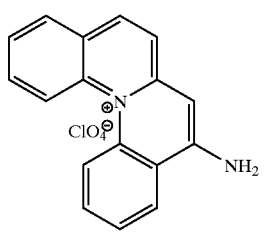

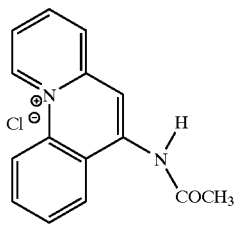

(compound 23)

(compound 24)

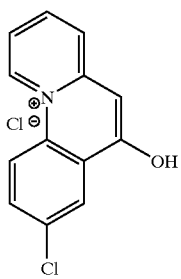

(compound 25 or MPB-30)

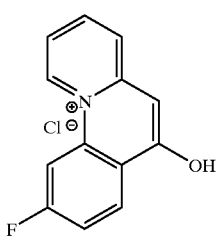

(compound 26 or MPB-29)

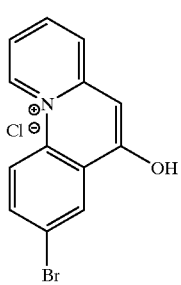

(compound 27 or MPB-32)

More particularly the invention relates to the use as described above, of compounds of general formula (IIIb) which follows:

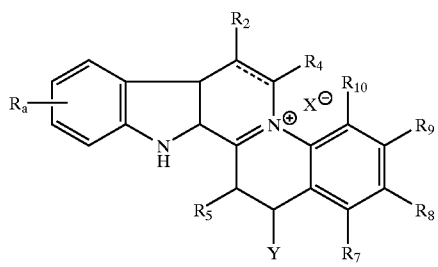

(IIIb)

in which $R_3$, $R_1$, $R_2$, $R_5$, $R_7$, $R_8$, $R_9$, $R_{10}$, X and Y are as defined above, and in particular the compounds of formula (IIIb) in which:

$R_a$ represents a hydrogen atom, $R_1$ and $R_2$ represent a hydrogen atom, and there is no double bond between the two carbons carrying $R_1$ and $R_2$, $R_5$ represents a hydrogen atom, $R_7$, $R_8$, $R_9$, and $R_{10}$ represent a hydrogen atom, or one of $R_7$, $R_8$, $R_9$, and $R_{10}$ represents a halogen atom, in particular a chlorine, bromine or fluorine atom.

Y represents —$NH_2$,

X represents a halogen atom in anionic form, in particular a bromine atom $Br^-$, or a chlorine atom $Cl^-$, or a group of atoms in anionic form, in particular a perchlorate $ClO_4^-$, The compounds of formula (IIIb) advantageously used within the scope of the present invention, are those chosen from the following:

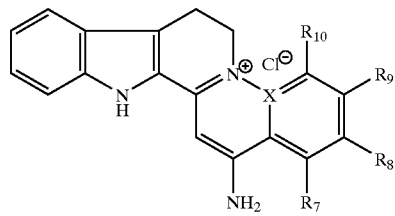

compound G: $R_7$=Cl, $R_8$=$R_9$=$R_{10}$=H⁻, compound H: $R_7$=$R_8$=$R_9$=$R_{10}$=H, compound I: $R_8$=Cl, $R_7$=$R_9$=$R_{10}$=H, compound J: $R_9$=Cl, $R_7$=$R_8$=$R_{10}$=H, compound K: $R_1$=Cl, $R_7$=$R_8$=$R_9$=H, compound L: $R_9$=Br, $R_7$=$R_8$=$R_{10}$=H.

A subject of the invention is any pharmaceutical composition containing, as active ingredient(s), at least one of the compounds of general formula (I) described above, in combination with a physiologically acceptable vehicle.

A more particular subject of the invention is an%, pharmaceutical composition as described above containing, as active ingredient(s), at least one of the compounds of formula (II) and more particularly of formula (IIa), as described above, and in particular at least one of compounds 1 to 10 described above, and even more particularly of formula (IIb), as defined above, and in particular at least one of compounds A to F described above.

A more particular subject of the invention is any pharmaceutical composition as described above containing, as active ingredient(s), at least one of the compounds of general formula (III) and more particularly of formula (IIIa), described above, and in particular at least one of compounds 11 to 27 described above, and even more particularly of formula (IIIb), as defined above, and in particular at least one of compounds G to L described above.

Preferred pharmaceutical compositions of the invention are those containing compound 19 (also designated MPB-07), if appropriate in combination with one (or more) other compound(s) of the invention described above.

Advantageously, the pharmaceutical compositions according to the invention are presented in a form which can be administered by oral route, in particular in the form of tablets or capsules, or in a form which can be administered by parenteral route, in particular in the form of preparations which are injectable by intravenous, intramuscular or subcutaneous route, or also via the airways, in particular by pulmonary route in the form of aerosols.

Yet more advantageously, the pharmaceutical compositions according to the invention are characterized in that the quantities of active ingredient(s) are such that the daily dose of active ingredient(s) is approximately 0.1 mg/kg to 5 mg/kg, in particular approximately 3 mg/kg, in one or more doses.

The invention also relates to the compounds of general formula (I) described above, as such, with the exception of compounds 2, 3, 9, 10, 11 (or MPB-26), 12 or (MPB-5), 22, 23 and 24 described above.

More particularly a subject of the invention is the compounds of general formula (I) described above, in which n=1, and corresponding to the compounds of general formula (II) described above, with the exception of compounds 2,3,9 and 10.

More particularly the invention relates to the compounds of general formula (Ia) described above, of which in particular compounds 1, 4, 5, 6, 7 and 8 described above.

More particularly the invention also relates to the compounds of general formula (IIa) described above, of which in particular compounds A to F described above.

More particularly a subject of the invention is the compounds of general formula (I) described above, in which n=0, and corresponding to the benzo[c]quinolizinium derivatives of formula (III) described above, with the exception of compounds 11, 12, 22, 23 and 24.

More particularly the invention relates to the compounds of general formula (IIIa) described above, of which in particular compounds 13, 14, 15, 16, 17, 18, 19, 20, 21, 25, 26 and 27 described above.

More particularly the invention also relates to the compounds of general formula (IIIb) described above, of which in particular compounds G to L described above.

A subject of the invention is also a preparation process for the compounds of general formula (I), characterized in that it includes the following steps:

treatment of the derivative of formula (A) in which $R_1$, $R_2$, $R_3$, $R_4$ and $R_5$ are as described in formula (I), with phenyllithium or lithium diisopropyl amide, advantageously in ether or THF, which leads to the obtaining of derivatives of formula (B) in which $R_1$, $R_2$, $R_3$, $R_4$ and $R_5$ are as described in formula (I), according to the following reaction diagram:

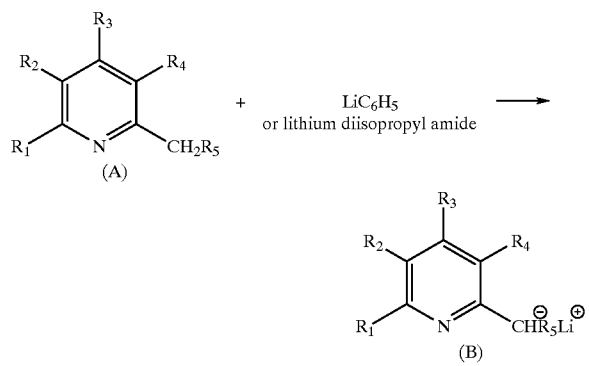

condensation of the derivative of formula (B) obtained in the previous stage with the derivative of formula (C) in which $R_7$, $R_8$, $R_9$, $R_{10}$ and X are as defined in formula (I), which leads to the obtaining of derivatives of formula (B) in which $R_1$, $R_2$, $R_3$, $R_4$, $R_5$, $R_7$, $R_8$, $R_9$, $R_{10}$ and X are as defined in formula (I), according to the following reaction diagram:

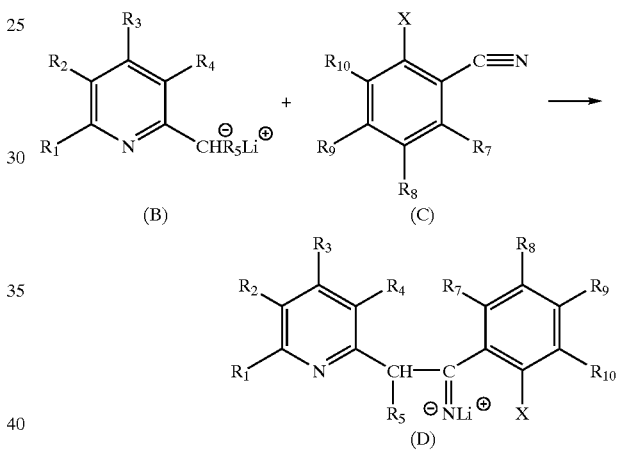

treatment of the compound of formula (D) by the addition of $H_2O$, which leads to the obtaining of the following derivative of formula (II), corresponding to a derivative of formula (II) described above, in which $R_1$ to $R_5$, $R_7$ to $R_{10}$, and X are as defined in formula (I), and Y represents —$NH_2$,

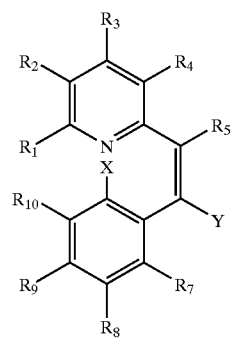

if appropriate, treatment of the above-mentioned compound of formula (II), with a derivative containing the $R_e$ and $R_f$ groups as defined in formula (I), this derivative being capable of reacting with the nitrogen atom linked to the carbon in position 6 of the above-mentioned compound of formula (II), in particular by a halide of $R_e$ and/or $R_f$ while having, if necessary, taken care to protect beforehand those other functions present on the above-mentioned compound of formula (II) and capable of reacting with the derivative containing the above-mentioned $R_e$ and $R_f$ groups, which leads to the obtaining of the following compound of formula (II) in which $R_1$ to $R_5$, $R_7$ to $R_{10}$ and X are as defined above and Y represents an —$NR_eR_f$ group as defined in formula (I),

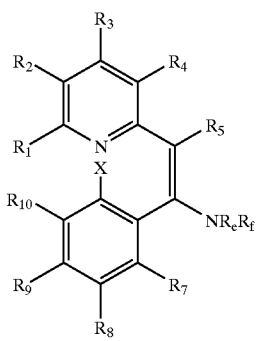

if appropriate, hydrolysis, in particular by the action of sulphuric acid (pH3) at 40° C., of the above-mentioned compound of formula (II) in which Y represents $NH_2$, which leads to the obtaining of the following compound of formula (II), corresponding to a derivative of formula (II) described above, in which $R_1$ to $R_5$, $R_7$ to $R_{10}$ and X are as defined in formula (I), and Y represents an —OH group,

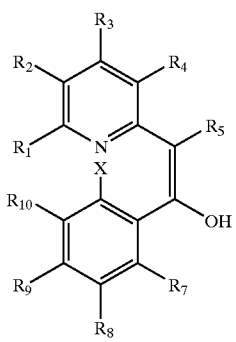

if appropriate, treatment of the above-mentioned compound of formula (II), in which Y represents an —OH group, with a derivative containing the $R_d$ group, as defined in formula (I), this derivative being capable of reacting with the oxygen atom 71 linked to the carbon in position 7 of the above-mentioned compound of formula (II), in particular by a halide of $R_d$, while having, if necessary, taken care to protect beforehand those other functions present on the above-mentioned compound of formula (II) and capable of reacting with the derivative containing the above-mentioned $R_d$ group, which leads to the obtaining of the following compound of formula (II) in which $R_1$ to $R_5$, $R_7$ to $R_{10}$ and X are as defined above and Y represents an —$OR_d$ group as defined in formula (I),

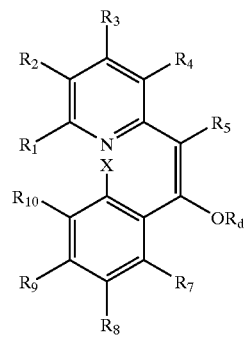

if appropriate, heating, advantageously at 200° C., the above-mentioned compounds of formula (II) in which Y represents —$NH_2$ or —OH, which leads respectively to the following compounds of formula (III) described above, corresponding to the compounds of formula (III) described above, in which $R_1$ to $R_5$, $R_7$ to $R_{10}$ and X are as defined in formula (I) and Y represents an —$NH_2$ or —OH group,

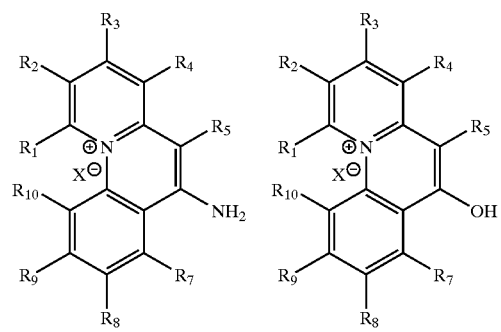

if appropriate, treatment of the above-mentioned compound of formula (III), in which Y represents an —$NH_2$ group, with a derivative containing the $R_e$ and $R_f$ groups as defined in formula (I), this derivative being capable of reacting with the nitrogen atom linked to the carbon in position 6 of the above-mentioned compound of formula (III), in particular by a halide of $R_e$ and/or $R_f$ while having, if necessary, taken care to protect beforehand those other functions present on the above-mentioned compound of formula (III) and capable of reacting with the derivative containing the above-mentioned $R_e$ and $R_f$ groups, which leads to the obtaining of the following compound of formula (III) in which $R_1$ to $R_5$, $R_7$ to $R_{10}$ an X are as defined above and Y represents an —$NR_eR_f$ group as defined in formula (I),

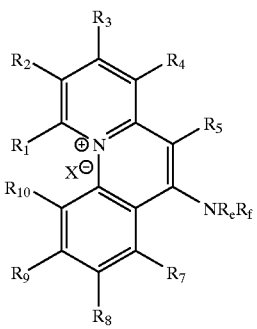

if appropriate, treatment of the above-mentioned compound of formula (III), in which Y represents an —OH group, with a derivative containing the $R_d$ group, as defined in formula (I), this derivative being capable of reacting with the oxygen atom linked to the carbon in position 7 of the above-mentioned compound of formula (III), in particular by a halide of $R_d$, while having, if necessary, taken care to protect beforehand those other functions present on the above-mentioned compound of formula (III) and capable of reacting with the derivative containing the above-mentioned $R_d$ group, which leads to the obtaining of the following compound of formula (III) in which $R_1$ to $R_5$, $R_7$ to $R_{10}$ and X are as defined above and Y represents an —$OR_4$ group as defined in formula (I),

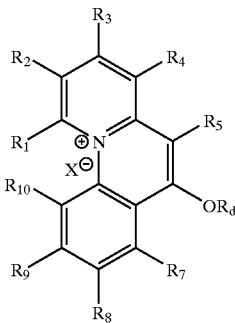

if appropriate, hydrogenation of the above-mentioned compounds of formulae (II) or (III), in particular by catalytic hydrogenation in the presence of platinum oxide at reduced pressure, which leads to the obtaining of the following compounds of formulae (II) or (III):

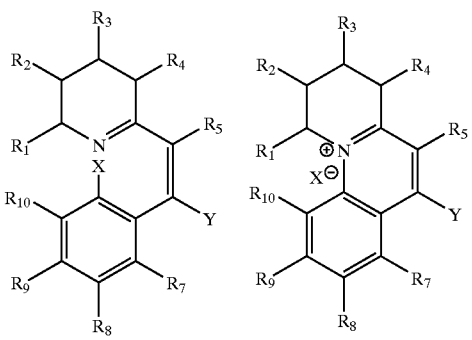

in which $R_1$ to $R_5$, $R_7$ to $R_{10}$, X and Y are as defined above.

Compounds A to L described above are advantageously obtained by the treatment of harmalane with butyl lithium (BuLi, 2 eq.) at −40° C., then the addition of 2-chlorobenzonitrile (if appropriate substituted by one or more $R_7$, $R_8$, $R_9$ and $R_{10}$ groups as defined above), which leads to the obtaining of the compounds of formula A to F which, by heating at 195° C., under nitrogen, leads respectively to compounds G to L.

The invention will be further illustrated using the detailed description which follows of preparation processes for compounds 1 to 24 described above, as well as the study of the effects of certain of these compounds on CFTR.

I—Preparation Processes for Compounds 1 to 24 a) 1-Hydroxy, 1-Phenyl, 2-(2-Pyridyl)ethylene (Compound 1)

Compound 1 is prepared according to any operating method identical to that described hereafter within the scope of the preparation of compound 2, but using benzonitrile instead of 2-chlorobenzonitrile.

b) 1-Hydroxy, 1-(2-Chlorophenyl, 2-(2-Pyridyl)ethylene (Compound 2)

2.22 g (0.022 mole) of diisopropylamine in 30 ml of anhydrous THF is placed in a 500 ml reactor, equipped with, a reflux condenser with a calcium chloride drying tube and a supply of nitrogen. The solution is taken to 0° C., then 13.75 ml of BuLi in solution at 1.6M of hexane (0.022 mole) is added. Agitation is carried out for 30 minutes at 0° C., then the temperature is lowered to −40° C., then 1.86 g (0.02 mole) of 2-methylpyridrine is added. Agitation is carried out for 30 minutes at −40° C., then 2.75 g of 2-chlorobenzonitrile in 20 ml of anhydrous THF is added. The reaction medium is left to return to ambient temperature and 20 ml of water is added, then the pH is adjusted to 2 be the addition of 2N $H_2SO_4$. Heating under reflux is carried out under agitation for 1 hour, followed by extraction with chloroform and drying over sodium sulphate. The solvent is evaporated off and the residue dissolved in the minimum amount of anhydrous ether, then ethanol saturated with HCl is added dropwise until the complete precipitation of the hydrochloride. In this way 2.99 g of compound 2 is obtained i.e, a yield of 56%.

Melting point (M.p.) = 190° C.
Elementary analysis: $C_{13}H_{11}ClN_2O$

| | | | |
|---|---|---|---|
| Calculated % | C: 58.20 | H: 4.10 | N: 5.20 |
| Found % | C: 58.00 | H: 4.10 | N: 5.30 | c) 1-Amino, 1-(2-Chlorophenyl, 2-(2-Pyridyl)ethylene (Compound 3)

Compound 3 is prepared according to any operating method identical to that described above within the scope of the preparation of compound 2, but without the hydrolysis stage by the addition of $H_2SO_4$.

d) 1-Hydroxy, 1-(2-Bromophenyl, 2-(2-Pyridyl)ethylene (Compound 4)

Compound 4 is prepared according to any operating method identical to that described above within the scope of the preparation of compound 2, but using 2-benzobenzonitrile instead of 2-chlorobenzonitrile.

e) 1-Hydroxy, 1-(2,3-Dichlorophenyl, 2-(2-Pyridyl)ethylene (Compound 5)

2.22 g (0.022 mole) of diusopropylamine in 30 ml of anhydrous THF is placed in a 500 ml reactor, equipped with a reflux condenser with a calcium chloride drying tube and a supply of nitrogen. The solution is taken to 0° C., then 13.75 ml of BuLi in solution at 1.6M of hexane (0.022 mole) is added. Agitation is carried out for 30 minutes at 0° C., then the temperature is lowered to −40° C., then 1.86 g (0.02 mole) of 2-methylpyridrine is added. Agitation is carried out for 30 minutes at −40° C., then 2.58 g (0.015 mole) of 2,3-dichlorobenzonitrile in 20 ml of anhydrous THF is added. The reaction medium is left to return to ambient temperature and 20 ml of water is added, then the pH is adjusted to 2 by the addition of 2N $H_2SO_4$. Heating under reflux is carried out under agitation for 2 hours, followed by separation of the organic phase and drying over sodium sulphate. The solvent is evaporated off and the residue is chromatographed on a silica column eluting with chloroform in order to obtain 3.19 g (80%) of pure ketone.

| Melting point (M.p.) = 112° C. | | | |
|---|---|---|---|
| Elementary analysis: $C_{13}H_9NOCl_2$ | | | |
| Calculated % | C: 58.67 | H: 3.41 | N: 5.26 |
| Found % | C: 58.53 | H: 3.63 | N: 5.34 |

$^1$H NMR spectrum ($CDCl_3$) (δ ppm, signal, N protons, attribution): 8, doublet, H in position 6 of pyridine: 7,6,5, multiplet, 6, aromatic H's. 5.55, s, b (80%) vinylic H: 4.25, s s2 (20%) $CH_2$.

The base obtained in this way can be converted into the hydrochloride: the base is dissolved in anhydrous ether and anhydrous ethanol saturated with HCl is added dropwise.

| Elemental analysis: $C\_H_{10}Cl_3$ | | | |
|---|---|---|---|
| Calculated % | C: 51.60 | H: 3.33 | N: 4.63 |
| Found % | C: 51.75 | H: 3.52 | N: 4.58 | f) 1-Hydroxy, 1-(2,4-Dichlorophenyl), 2-(2-Pyridyl) ethylene (Compound 6)

Compound 6 is prepared according to any operating method identical to that described above within the scope of the preparation of compound 2, but using 2-4-dichlorobenzonitrile instead of 2-chlorobenzonitrile.

g) 1-Hydroxy, 1-(2,5-Dichlorophenyl), 2-(2-Pyridyl) ethylene (Compound 7)

Compound 7 is prepared according to any operating method identical to that described above within the scope of the preparation of compound 2, but using 2-5-dichlorobenzonitrile instead of 2-chlorobenzonitrile.

h) 1-Hydroxy, 1-(2,6-Dicholorphenyl), 2-(2-Pyridyl) ethylene (Compound 8)

Compound 8 is prepared according to any operating method identical to that described above within the scope of the preparation of compound 2, but using 2-6-dichlorobenzonitrile instead of 2-chlorobenzonitrile.

i) 1-Hydroxy, 1-(2-Chlorophenyl), 2-(2-Quinonyl)ethylene (Compound 9)

Compound 9 is prepared according to any operating method identical to that described above within the scope of the preparation of compound 2, but using 2-methylquinoline instead of 2-methylpyridine.

j) 1-Amino, 1-(2-Chlorophenyl, 2-(2-Quinolyl)ethylene (Compound 10)

Compound 10 is prepared according to any operating method identical to that described above within the scope of the preparation of compound 9, but without the hydrolysis stage by the addition of $H_2SO_4$.

k) 6-Aminobenzo[c]quinolizium MPB-26 (Compound 11)

2.22 g (0.022 mole) of diusopropylamine in 30 ml of anhydrous THF is placed in a 500 ml reactor, equipped with a reflux condenser with a calcium chloride drying tube and a supply of nitrogen. The solution is taken to 0° C., then 13.75 ml of BuLi in solution at 1.6M in hexane (0.022 mole) is added. Agitation is carried out for 30 minutes at 0° C., then the temperature is lowered to −40° C., then 1.86 g (0.02 mole) of 2-methylpyridrine is added. Agitation is carried out for 30 minutes at −40° C., then 2.75 g of 2-chlorobenzonitrile (0.02 mole) in 20 ml of anhydrous THF is added. The reaction medium is left to return to ambient temperature and a 10% solution of ammonium chloride is added. The organic phase is separated, dried over $Na_2SO_4$, evaporated and the residue is taken to 200°° C., under a current of nitrogen for 15 minutes. The evolution of a white vapour is observed and the residue solidifies to a brownish mass. The product is purified by a first washing with acetone then dissolution in ethanol and precipitation with ethyl acetate. Purification can also be carried out with chromatography on a neutral alumina column eluting with ethyl acetate. In this way 1.73 g (35%) of product is obtained crystallizing with one molecule of water.

| Melting point (M.p.) = decomposition at approx. 280° C. | | | |
|---|---|---|---|
| Elementary analysis: $C_{13}$ $H_{13}C_1N_2O$ ($C_{13}$ $H_{11}C_1N_2$, $H_2O$) | | | |
| Calculated % | C: 62.78 | H: 5.27 | N: 11.26 |
| Found % | C: 62.86 | H: 5.03 | N: 11.25 |
| Mass spectrum: m/e 194 ($M^+$—HCl—$H_2O$). | | | |
| Infrared spectrum (KBr) (ν $cm^{-1}$, attribution): 3460, 3360, | | | |
| $NH_2$: 1660, 1640, 1660, 1640, 1660, C=N, | | | |
| C=C: 760 orthosubstituted benzene. | | | |

$^1$H NMR spectrum (DMSOd6) (δ ppm, signal, n protons, attribution): 3.2 to 4 exchangeable peak $D_2O$ ($NH_2$+$H_2O$); 7.1 singlet, H in position 5: 7.4 to 8.15, 2 massives, aromatic 5H's: 9.00, 2H, aromatics; 9.8, doublet J=8 Hz, H in position 1.

l) 6-Hydroxybenzo[c]quinolizinium Chloride MPB-05 (Compound 12)

1-hydroxy, 1-(2-chlorophenyl), 2-(2-pyridyl)ethylene (compound 2) is neutralized with an aqueous solution of sodium carbonate, the base is extracted with ether, the solution is dried over $Na_2SO_4$ then the solvent is evaporated off, 1.16 g (0.005 mole) of base in the form of a pale yellow oil is heated under nitrogen at 195° C. for 15 minutes. The residue thus obtained is washed with acetone, then dissolved in ethanol and precipitated by the addition of ethyl acetate, 0.75 g (60%) of product is obtained crystallized with one molecule of water and with a creamy white colour.

| Melting point (M.p.) = 256° C. (decomposition) | | | |
|---|---|---|---|
| Elementary analysis: $C_{13}H_{10}ClNO$, $H_2O$ i.e. $C_{13}H_{12}ClNO$ | | | |
| (M = 231.5 + 18 = 249.5) | | | |
| Calculated % | C: 62.53 | H: 4.85 | N: 5.61 |
| Found % | C: 62.40 | H: 5.00 | N: 5.80 |
| Mass spectrum: m/e 195 ($M^-$—HCl—$H_2O$), | | | |
| 167 ($M^+$—HCl—$H_2O$—CO). | | | |
| Infrared spectrum (KBr) (ν $cm^{-1}$, attribution): 3250, | | | |
| OH: 1640, C=N, 770 orthosubstituted benzene. | | | |

$^1$H NMR spectrum (DMSOd6) (δ ppm, signal, n protons, attribution):

6.60 broad exchangeable peak $D_2O$, HO; 7.75, singlet, H in position 5: 7.9 to 18.6, multiplet, 6H aromatics: 9.15 doublet, J=6.5 Hz, 1H: 10, doublet, J=6 Hz, H in position 1.

m) 6-Aminobenzo[c]quinolizinium Bromide MPB-01 (Compound 13):

Compound 13 is prepared according to any operating method identical to that described above within the scope of the preparation of compound 11, but using 2-bromobenzonitrile instead of 2-chlorobenzonitrile.

n) 6-Amino, 10-chlorobenzo[c]quinolizinium Chloride MPB-02 (Compound 14):

Compound 14 is prepared according to any operating method identical to that described above within the scope of the preparation of compound 11, but using 2,3-dichlorobenzonitrile instead of 2-chlorobenzonitrile, o) 6-Amino, 9-Chlorobenzo[c]quinolizinium Chloride (Compound 15):

Compound 15 is prepared according to any operating method identical to that described above within the scope of the preparation of compound 11, but using 2,4-dichlorobenzonitrile instead of 2-chlorobenzonitrile.

p) 6-Amino, 7-Chlorobenzo[c]quinolizinium Chloride (Compound 16):

Compound 16 is prepared according to any operating method identical to that described above within the scope of the preparation of compound 11, but using 2.6-dichlorobenzonitrile instead of 2-chlorobenzonitrile.

q) 6-Amino, 8-Chlorobenzo[c]quinolizinium Chloride (Compound 17):

Compound 17 is prepared according to any operating method identical to that described above within the scope of the preparation of compound 11, but using 2,5-dichlorobenzonitrile instead of 2-chlorobenzonitrile.

r) 6-Hydroxbenzo[c]quinolizinium Bromide MPB-06 (Compound 18):

Compound 18 is prepared according to any operating method identical to that described above within the scope of the preparation of compound 19, but is carried out starting from compound 4 instead of compound 5.

s) 6-Hydroxy, 10-Chlorobenzo[c]quinolizinium Chloride MPB-07 (Compound 19):

1.40 g (0.0053 mole) of 1-hydroxy, 1-(2-bromophenyl), 2-(2-pyridyl)ethylene (compound 5) is heated under nitrogen at 215° C. At around 190°° C. the appearance of white fumes of HCl is noted and heating is continued at 220°° C. for 10 minutes. The product is washed with chloroform then the residue (1.82 g) is purified by chromatography on a silica column eluting with acetate and alcohol. In this way 0.58 g (42%) of product is obtained.

Melting point (M.p.) = 196° C. (decomposition)
Elementary analysis: $C_{13}H_{10}NOCl_2$
Calculated %   C: 56.75   H: 3.66   N: 4.63
Found %        C: 56.25   H: 3.31   N: 4.78 t) 6-Hydroxy, 9-Chlorobenzo[c]quinolizinium Chloride MPB-08 (Compound 20):

Compound 20 is prepared according to any operating method identical to that described above within the scope of the preparation of compound 19, but is carried out starting from compound 6 instead of compound 5.

u) 6-Hydroxy, 7-Chlorobenzo[c]quinolizinium Chloride (Compound 21):

Compound 21 is prepared according to any operating method identical to that described above within the scope of the preparation of compound 19, but is carried out starting from compound 8 instead of compound 5.

v) 8-Aminodibenzo[c.f]quinolizinium Perchlorate (Compound 22):

2.22 g (0.022 mole) of diusopropylamine in 30 ml of anhydrous THF is placed in a 500 ml reactor, equipped with a reflux condenser with a calcium chloride drying tube and a supply of nitrogen. The solution is taken to 0° C., then 13.75 ml of BuLi in solution at 1.6M in hexane (0.022 mole) is added. Agitation is carried out for 30 minutes at 0° C. then the temperature is lowered to −40° C. then 2.86 g (0.02 mole) of quinaldine is added. Agitation is carried out for 30 minutes at −40° C., then 2.75 g of 2-chlorobenzonitrile (0.02 mole) in 20 ml of anhydrous THF is added. The reaction medium is left to return to ambient temperature and a 10% solution of ammonium chloride is added. The organic phase is separated, dried over $Na_2SO_4$, evaporated and the residue is taken to 230° C. under a current of nitrogen for 30 minutes. The evolution of a white hydrochloric acid vapour is observed and the residue solidifies to a brownish mass. The product is purified by a first washing with acetone then dissolution in ethanol and precipitation with ethyl acetate. The product is dissolved in a minimum amount of water and a solution of perchloric acid is added until precipitation is complete. The compound is filtered out in order to recover 2.20 g (32%).

Elementary analysis: $C_{17}H_{13}ClN_2O_4$
Calculated %   C: 59.22   H: 3.80   N: 8.13
Found %        C: 59.39   H: 3.95   N: 8.26
Infrared spectrum (KBr) (v cm$^{-1}$, attribution): 3400, 3280,
$NH_2$: 1650, 1600, 1000, broad band, $ClO_4$ $^1$H NMR spectrum (DMSOd6) (δ ppm, signal, n protons, attribution): 7.0, singlet, 1H in position 5; 7.5 to 8.7, multiplet, aromatic 10H's: 9.0 singlet, 2H, exchangeable $D_2O$.

w) 6-Acetoamidobenzo[c]quinolizinium Chloride (Compound 23)

1 g (0.004 mole) of 6-aminobenzo[c]quinolizinium is dissolved in 10 ml of acetic acid, then 25 ml of acetic anhydride is added. The reaction medium is taken to reflux for 24 hours, then the acetic anhydride and acetic acid is evaporated off under reduced pressure.

The product obtained has a violet colour and is washed with ethyl acetate, then recrystallized from ethanol, 0.93 g (85%) of a creamy white product is obtained.

M.p.=>280° C.;

Elementary analysis: $C_{15}H_{13}ClN_2O$
Calculated %   C: 66.05   H: 4.80   N: 10.27
Found %        C: 65.85   H: 5.01   N: 10.3
Infrared spectrum (KBr) (v cm$^{-1}$, attribution): 3450,
NH: 1700, C=O.

x) 1,2,3,4-Tetrahydro, 6-Aminobenzo[c,f]quinolizinium Perchlorate (Compound 24):

0.50 g (0.002 mole) 6-aminobenzo[c]quinolizinium hydrochloride is dissolved in 20 ml of ethanol and is placed in the presence of platinum oxide and hydrogen at atmospheric pressure. Hydrogenation is carried out over a few minutes then the solution is filtered, the alcohol is evaporated off and the residue is taken up in 10 ml of distilled water and a 25% solution of perchloric acid is added while the precipitate forms. The white product is recrystallized from methanol in order to produce 0.54 g (91%) of perchlorate.

M.p. = 240° C.
Elementary analysis: $C_{13}H_{15}ClN_2O_4$
Calculated %   C: 52.27   H: 5.06   N: 9.38
Found %        C: 52.30   H: 5.16   N: 9.46
Infrared spectrum (KBr) (ν cm$^{-1}$, attribution): 3460, 3360, NH$_2$: 1650, 1600, 1100, broad band, ClO$_4$.

$^1$H NMR spectrum (DMSOd6) (δ ppm, signal, n protons, attribution):
2.1, multiplet. CH$_2$ in position 2 and 3; 3.20, triplet, CH, in position 4: 4.45, triplet, CH$_2$ in position 1; 6.60, singlet. H in position 5; 7.6 to 8.4, multiplet, 4H, aromatics; 8.6 singlet, 2H, exchangeable D$_2$O.

II—Preparation Process for Compounds A to F a) 1-Amino 1-(2,6-Dichlorophenyl) 2-[1-(3,4-Dihydropyrido[3-4-b]indolyl)]ethylene (Compound A)

1.84 g (0.01 mole) of harmalane is solubilized in 40 ml of THF in a reactor equipped with a nitrogen supply and the reaction medium is taken to −40° C., 13.75 ml (0.022 mole) of BuLi is added dropwise, a dark red colouring appears, the solution is left under agitation for 30 minutes, 1.71 g (0.01 mole) of 2,6-dichlorobenzonitrile is solubilized in 15 ml of THF, then added dropwise. After 1 hour at −40° C., the mixture is agitated for 4 hours at room temperature. The development of the reaction is monitored by TLC, the disappearance of the starting products is correlated to the appearance of a yellow fluorescent spot characteristic of the imine. Hydrolysis with 5 ml of a 10% solution of NH$_4$Cl allows the THF phase containing the imine to be recovered. This phase is dried over Na$_2$SO$_4$, filtered then evaporated to dryness. The product is purified by column chromatography on silica gel, eluting with a CH$_2$Cl$_2$/CH$_3$COOC$_2$H$_5$ 5% mixture. In this way 2.06 g of compound A is obtained, i.e, a yield of 58%.

M.p. = 228° C.
Elementary analysis: $C_{19}H_{15}N_3Cl_2$
Calculated %   C: 64.06   H: 4.24   N: 11.79
Found %        C: 64.21   H: 4.37   N: 11.62

Infrared spectrum (KBr) (ν cm$^{-1}$, attribution): 3428, 3255, 3134 cm$^{-1}$. NH: NH$_2$; 3134 cm$^{-1}$, C=C—H; 2932, 2843 cm$^{-1}$, CH$_2$; $^1$H NMR spectrum (DMSOd6) (δ ppm, signal, n protons, attribution): 8.40 singlet exchangeable by D$_2$O, 3 H, NH and NH$_2$; 7.20, multiplet, 7 H, aromatic protons; 5.00, singlet, 1H, vinylic H; 3.70, triplet, J=6 Hz, 2 H, CH$_2$; 3.00, triplet, J=6 Hz, 2 H, CH$_2$.

b) 1-Amino 1-(O-chlorophenyl) 2-[1-(3,4-Dihydropyrido[3-4-b]indolyl)]ethylene (Compound B)

Compound B is prepared according to any operating method identical to that described above within the scope of the preparation of compound A, but using orthochlorobenzonitrile instead of 2,6-dichlorobenzonitrile.

c) 1-Amino 1-(2,5-Dichlorophenyl) 2-[1-(3,4-Dihydropyrido[3-4-b]indolyl)]ethylene (Compound C)

Compound C is prepared according to any operating method identical to that described above within the scope of the preparation of compound A, but using 2,5-dichlorobenzonitrile instead of 2,6-dichlorobenzonitrile.

d) 1-Amino 1-(2,4-Dichlorophenyl) 2-[1-(3,4-Dihydropyrido[3-4-b]indolyl)]ethylene (Compound D)

Compound D is prepared according to any operating method identical to that described above within the scope of the preparation of compound A, but using 2,4-dichlorobenzonitrile instead of 2,6-dichlorobenzonitrile.

e) 1-Amino 1-(2,3-Dichlorophenyl) 2-[1-(3,4-Dihydropyrido[3-4-b]indolyl)]ethylene (Compound E)

Compound E is prepared according to any operating method identical to that described above within the scope of the preparation of compound A, but using 2,3-dichlorobenzonitrile instead of 2,6-dichlorobenzonitrile.

f) 1-Amino 1-(4-Bromo, 2-Chlorophenyl) 2-[1-(3,4-Dihydropyrido[3-4-b]indolyl)]ethylene (Compound F)

Compound F is prepared according to any operating method identical to that described above within the scope of the preparation of compound A, but using 2-chloro-4 bromobenzonitrile instead of 2,6-dichlorobenzonitrile.

III—Production Process for Compounds G to L

Cyclization of compounds A to F into quinolizinium G to L.

a) 14-Amino 6,7-Dihydro 12H-1-Chloro Benzo-[n]indolo[2,3-a]quinolizinium Chloride (Compound G).

Purified enamine A is heated under nitrogen; this product liquefies at about 150° C., then at 195°° C. white fumes appear and the product solidifies. Heating is maintained at this temperature for 10 minutes. The following is observed using TLC: disappearance of the yellow fluorescent spot of the imine with an Rf of 0.3 on silica in CH$_2$Cl$_2$ and the appearance of a yellow-green fluorescent spot of the cyclized product with an Rf of 0.1 on alumina in alcohol. The product is purified by washing with acetone, then recrystallization from alcohol or by chromatography: alumina—alcohol.

The product thus obtained has a light brown colour, with a yield of 17%.

M.p. = 228° C.
Elementary analysis: $C_{19}H_{15}N_3Cl_2$, ½ H$_2$O
Calculated %   C: 62.48   H: 4.41   N: 11.50
Found %        C: 62.29   H: 4.47   N: 11.43

$^1$H NMR spectrum (CF$_3$COOD) (δ ppm, signal, n protons, attribution): 8.10–6.20, massive, 11 H, aromatic protons+NH+NH$_2$; 3.90, triplet poorly resolved, 2 H, CH$_2$ in position 6; 3.00, triplet poorly resolved, 2 H, CH$_2$ in position 7; Infrared spectrum (KBr) (ν cm$^{-1}$, attribution) presenting all the same absorptions: 3458, 3371 cm$^{-1}$, NH: NH$_2$; 3073 cm$^{-1}$; C=C—H; 1638 cm$^{-1}$, C=N, C=C.

b) 14-Amino 6,7-Dihydro 12H-Benzo-[f]indolo[2,3-a]quinolizinium Chloride (Compound H).

Compound H is prepared according to any operating method identical to that described above within the scope of the preparation of compound G, but using compound B instead of compound A.

The product obtained has a mustard yellow colour with a yield of 56%.

M.p. = greater than 260° C.
Elementary analysis: $C_{19}H_{16}N_3Cl$
Calculated %   C: 70.91   H: 5.01   N: 13.06
Found %        C: 70.33   H: 5.06   N: 12.71 c) 14-Amino 6,7-Dihydro 12H-2-Chloro Benzo-[1]indolo[2.3-a]quinolizinium Chloride (Compound I).

Compound I is prepared according to any operating method identical to that described above within the scope of the preparation of compound G, but using compound C instead of compound A.

The product obtained has a light brown colour with a yield of 7%.

M.p. = greater than 260° C.
Elementary analysis: $C_{19}H_{15}N_3Cl_2$, $H_2O$
Calculated %  C: 60.97  H: 4.38  N: 11.22
Found %  C: 61.32  H: 5.03  N: 10.52 d) 14-Amino 6,7-Dihydro 12H-3-Chloro Benzo-[1]indolo[2,3-a]quinolizinium Chloride (Compound J).

Compound J is prepared according to any operating method identical to that described above within the scope of the preparation of compound G, but using compound D instead of compound A.

The product obtained has a light brown colour with a yield of 52%.

M.p. = greater than 260° C.
Elementary analysis: $C_{19}H_{15}N_3Cl_2$
Calculated %  C: 64.06  H: 4.24  N: 11.79
Found %  C: 63.89  H: 4.48  N: 11.58 e) 14-Amino 6,7-Dihydro 12H-4-Chloro Benzo-[1]indolo[2,3-a]quinolizinium Chloride (Compound K).

Compound K is prepared according to any operating method identical to that described above within the scope of the preparation of compound G, but using compound E instead of compound A.

The product obtained has a light brown colour with a yield of 6%.

M.p. greater than 260° C.
Elementary analysis: $C_{19}H_{15}N_3Cl_2$, $H_2O$
Calculated %  C: 60.97  H: 4.58  N: 11.22
Found %  C: 60.56  H: 4.66  N: 10.84 f) 14-Amino 6,7-Dihydro 12H-3-Bromo Benzo-[1]indolo[2,3-a]quinolizinium Chloride (Compound L).

Compound L is prepared according to any operating method identical to that described above within the scope of the preparation of compound G, but using compound F instead of compound A.

The product obtained has a mustard yellow colour with a yield of 12%.

M.p. = greater than 260° C.
Elementary analysis: $C_{19}H_{15}N_3Cl$, Br, $2H_2O$
Calculated %  C: 52.25  H: 4.38  N: 9.62
Found %  C: 52.28  H: 4.36  N: 9.66

IV—Studs of the Effects of Compounds of the Invention on CFTR

A) Methodology a) Culture of Human Epithelial Cells and Recombinant CHO Cells:

Several types of cells are used for this study: the intestinal lines T84, Caco-2 and HT 29. Chinese hamster ovary (CHO-K1) cells were transfected with the aid of the vector pNUT (Tabcharani et al., 1991) with or without (control cells) incorporation of normal or mutated CFTR cDNA (Chang et al., 1993). The cells are kept in this specific medium and then inoculated at a low density on to glass slides and cultured at 37° C. (5% $CO_2$), before the patch clamping experiments. The survival medium of the cells is composed of αMEM with foetal calf serum (7%) and antibiotics: 50 IU/ml penicillin and 50 μg/ml streptomycin and methotrexate (100 μM to 200 μM).

b) Principles of the Technique of Molecular Electrophysiology or Patch Clamping:

The electrical activity of cells is controlled by the presence and functioning of transmembrane pores, the ion channels. The ion channels are proteins, the conformational state of which can be modified in response to various factors: the transmembrane electrical field, the binding of ligands or post-transcriptional biochemical reactions. The current passing through an ion channel is of the order of one billionth of an Ampère (pica-Ampère, 1 pA=$10^{-12}$ A). It can be measured by techniques of molecular electrophysiology, more commonly called patch clamping.

With the conventional techniques of measuring transmembrane currents by intracellular microelectrodes, the thermodynamic base noise is at least a hundred times greater than the current passing through a single ion channel. Under such conditions, the flow in a channel is masked by this noise, the variation of which increases with the mean current. Erwin Neher and Bert Sackman (see Hamill et al., 1981) of the Max Planck Institute of Göttingen have shown that by analysis of this noise, it was possible to estimate the current passing in an ion channel. The thermodynamic base noise is proportional to the area of the membrane. By limiting this, the base noise thus becomes lower than the current passing through the channel.

The patch clamping technique is derived from the observation made by these two researchers and their colleagues: a glass micropipette applied to a membrane surface adheres there such that the electrical resistance established between the pipette and the membrane reaches a gigaohm value (1 Gohm=$10^9$ ohm). Ohm's law gives the electrical resistance (R) with respect to the current intensity I (in Amperes) and the potential U (in volts) applied (equation 1) and enables the unit conductance (unit: the picoSiemens, ps) of the channel g to be determined (equation 2).

$$U=R.I \qquad \text{(equation 1)}$$

$$g=1/R \qquad \text{(equation 2)}$$

The interaction forces between the glass of the pipette and the phospholipids of the membrane enable the leakage currents to be reduced, an essential stage for measuring the current passing through an ion channel. The configuration obtained in this way is designated by the term "cell-attached". By withdrawing the pipette starting from the cell-attached configuration, a fragment (patch) of the membrane is torn away, and remains fixed on the end of the pipette. The configuration obtained in this way is called "inside-out", since the intracellular surface of the membrane is in the bath. The extracellular surface of the membrane is in contact with the solution contained in the pipette, while intracellular part is in contact with the perfusion medium of the experimental chamber. An electronic assembly allows application (clamping) of a potential difference (Vref–Vp) between the reference electrode of the bath (Vref) and the pipette (Vp) and measurement of the resultant current I. If the ionic composition is the same on both sides of the membrane (symmetric media), the current intensity I is then directly proportional to the potential difference applied to the membrane. The points I(V) are generally distributed along a straight line, the gradient and position of which define the unit conductance (g) of the channel and the reversal potential of the current, Erev. At the reversal potential, the flow of charges through the membrane is zero. The reversal potential will be defined by the Nernst equation (equation 3), where E represents the Nernst potential for the ion under consideration and C represents the concentration of the ion in the extracellular (Co) and intracellular (Ci) compartments.

$$E = RT/zF \log Co/Ci \qquad \text{(equation 3)}$$

In the cell-attached configuration, the potential of the electrode is added to that of the membrane, which is about −60 mV. In all the cells, the concentrations of potassium ($K^+$) and chlorine ($Cl^-$) ions are about 150 mM and 10 mM respectively. With a pipette containing 150 mM KCl, the Nernst potentials for the $K^+$ ($E_K$) and $Cl^-$ ($E_{Cl}$) ions will be close to zero and −50 mV respectively. The reversal of the chlorine current will therefore be obtained in the vicinity of the rest potential, that is to say without application of potential to the membrane (Vp=0 mV). On the other hand, the reversal of a potassium current will be obtained by cancelling the potential of the membrane, thus by depolarizing it by 50 to 60 mV. This example illustrates the strategies used to evaluate the ionic nature of a channel. The information collected by this technique is represented by the fluctuation in an electrical current (of millisecond order, ms), which conveys the transitions between the various states of conductance of the channel.

c) Patch Clamping Applied to the Study of Epithelial Cells in Culture.

The patch clamping experiments are carried out on confluent cells. A fragment of the glass slide (cell support) is placed in an experimental chamber (volume 600 μl or 1 ml) on the platen of an inverted microscope fitted with phase contrast illumination (Olympus IMT2). The cell-attached and inside-out configurations are used (Hamill et al., 1981). The experiments are carried out at room temperature (20–22° C.). The currents are amplified with a LIST EPC 7 amplifier (Darmstadt, Germany) (filter of 3 kHz) with a low-pass filter of 2–5 kHz (6-pole Bessel filter) and recorded with a DAT (digital audio tape) after digitalization (16 bits) at 44 kHz. The data are then transferred to an Olivetti M28PC computer. The pipettes are made from glass tubes of 1 mm diameter (Clarke Electromedical Instrument) in two or three stages with a horizontal drawer (Flaming/Brown type, model P-87. Sutter. Inst. Co. USA). The pipettes filled with a solution of 150 mM NaCl have a resistance of between 4 and 12 MΩ. The potentials are expressed as the difference between the potential of the patch electrode and that of the bath. In the cell-attached configuration, they represent the change in potential with respect to the rest potential of the cell. The diffusion potentials are evaluated from the potential of the electrode corresponding to a zero current (when the channels are closed). They are minimized using an agar bridge which establishes the connection between the bath and the reference electrode (earth) and contains the same solution as the pipette. The reversal potential of the current and the unit conductance of the channels are obtained from the current-voltage ratio (I/V) by linear regression. To determine the current-voltage ratio, the ionic current amplitudes are measured form amplitude histograms. The amplitude histograms are shown as the sum of two or more gaussian distributions, the peaks of which correspond to the open and closed states of channels present in the electrode. From these histograms it is possible to determine: N, the total number of channels present in the patch: n, the number of channels simultaneously open (n=0, 1, 2 . . . N): Po, the probability of opening of a channel: and I, the mean intensity of the current in a channel. If the channels present are of the same type and are assumed to open and close independently of one another, the probability of having n channels open simultaneously is given by the binomial distribution (equation 4), from which the individual probability Po is deduced (equation 5).

$$P(n) = (N!/n!(N-n)Po^n \cdot (1-Po)^{N-n} \qquad \text{(equation 4)}$$

$$Po = P(n)/N \qquad \text{(equation 5)}$$

Since the present study relates only to the $Cl^-$ channels, an exit current would have to be interpreted as a movement of $Cl^-$ ions exiting the pipette towards the intracellular medium of the cells or towards the perfusion medium. The relative permeability $P_X/P_{Cl}$ of anion $X^-$ with respect to $Cl^-$ ions has been used to evaluate the ion selectivity of channels in the inside-out configuration. The Goldman-Hodgkin-Katz equation (equation 6) links the ratio of the permeabilities as a function of the reversal potential (Erev) obtained experimentally and the respective concentrations of anions present.

$$\text{Erev} = -RT/F \ln ([Cl^-]_e + P_X/P_{Cl}[X^-]_e/[Cl^-]_i + P_X/P_{Cl}[X^-]_i) \qquad \text{(equation 6)}$$

i and e: intracellular and extracellular ion concentration. R. T and F have their usual meaning.

For filling the patch electrodes, the composition of the saline solutions is (in mM): 150 NaCl, 2 $MgCl_2$, 10 TES (pH 7.4). The perfusion bath of the cells contains (in mM): 145; NaCl, 4 KCl, 2 $MgCl_2$, 0.5 $CaCl_2$, 10 TES (pH 7.4).

d) Measurement of Short-circuit Currents in an Ussing Chamber.

The benefit of culture of epithelia in chambers with a permeable base, and in particular digestive epithelia (line HT 29 and it various clones, line T84 or Caco2) has been widely demonstrated in cell biology studies. In this technique, the cells are cultured inside a cup where the base is made of a membrane of polystyrene perforated with holes, the diameter (between 0.45 and 3 μm) and distribution of which are measured carefully. It enables attachment of cells without addition of a supplementary matrix. It is transparent in a medium of which the refractive index is close to that of water, and allows visual examination of the cell layer. However, there are limitations. Although the low thickness of the membrane limits retention of fluids, it cannot be ruled out that it may constitute a trap for macromolecules or complexes, such a gelosomes. This cup of 5 $cm^2$ surface area is placed in a 6-well plate. The attachment and the culture of the cells there are conducted in the traditional manner. A fortnight after the inoculation, the cells form an impervious monolayer. This imperviousness is proved by the occurrence of an electrical resistance or by non-diffusion of macromolecules between the two mucous and serous compartments. The culture is stable for about ten days, maintaining an identical culture medium in the two compartments. This culture of epithelia in chambers with a permeable base is quite useful for studying the nature and regulation of secretions and passages of charged or non-charged molecules through the epithelium. Transepithelial transportation will depend on the nature of the permeases present in the two apical or basolateral fields on either side of the clamped junction. The properties of the epithelium which manifests themselves by passage of charged molecules can be easily deduced from the measurement of the transepithelial potential or of the short-circuit current, lichen the molecules are neutral, labelled molecules are used to follow their movements.

e) Principles of the Measurement Method.

In outline, epithelial transportation is the balance of cell transportation and selective diffusion through the junction. Cell transportation results from the activity of pairs of specific permeases situated on the apical pole and on the basal pole of the cell respectively ($Na^+$ and $Na^+/K^+$ATPase channel. $Cl^-$ channel and $Na^+/K^+/Cl^-$ cotransporter, Na/glucose cotransporter and diffusional glucose transporter . . . ). When the transporter epithelium is impervious, the clamped junction isolates two parts of the membrane which have a different potential with respect to the medium. A simple electrical analogy can be used and they can be considered as circuit elements having the potentials Vm (mucous) and Vs (serous) respectively. These two membranes in series thus have a potential Vt which is the algebraic sum Vm+Vs. In the tissue used. Vt can reach −5 mV under standard conditions. To determine the characteristics of the epithelium, three types of measurement can be used.

Measurement by an Open Circuit.

The difference in potential existing on either side of the cell layer is measured. At a fixed time, a parametrable current i ($\mu$A) is sent into the circuit, which causes a change in the potential difference $\Delta$V proportional to the resistance of the circuit.

Measurement by a Short-circuit Current.

An adjustable current i which uses the resistance of the tissue to create a potential difference which will be added algebraically to that which exists is introduced into the circuit. When the current has the value Isc (short-circuit current). Vt is zero: Isc×Rt−Et=0 or Isc=Et/Rt. Under the conditions of Vm−Vs=0 and Vm=Vs, the two mucous and serous membranes are at the same potential. To determine the resistance, a given potential difference is applied to the circuit and the resistance is measured, evaluating the deviation in the current Isc which results.

Measurement by an Applied Voltage.

This is a particular case of the measurement by a short-circuit current, where this is applied to the epithelium to give a zero potential. Under these conditions, the transepithelial potential is fixed without knowing the potential of each of the membranes. For this, a potential difference is superimposed, prolonging the algebraic addition of the current used for measuring the resistance. A short time is chosen for the short-circuit current and a long time for the superimposed potential difference. It is clear that for a given resistance, the potential difference will depend on the capacity of the apparatus to deliver a maximum current (100 $\mu$A; for 500 ohms the potential difference is 50 mV), but also on the ability to measure the resultant potential difference (I V).

To carry out these measurements, the cups are mounted in a modified Ussing chamber. We use a "current-voltage clamp" (WPI) control unit, coupled to a pulse generator enabling the intensity/voltage curve to be plotted. The signal collected is digitalized (MacLab) and processed using Chart software on a Macintosh Apple computer.

f) Properties of the Epithelium Tested.

The epithelium formed by HT29 cells will first be used. The addition of glucose to the base medium (symmetric saline medium, absence of stimulator) in the mucous compartment causes an increase in the transepithelial potential and in the short-circuit current without affecting the resistance. The epithelium functions as a glucose absorber which utilizes an Na-dependent glucose transporter on the mucous side, and without doubt a diffusional transporter on the serous side. The transportation of sodium associated with glucose causes a potential difference, which can be inhibited by phlorizin, while the overall flow of glucose is measured with radiolabelled glucose analogues placed in the mucous or serous compartments.

The addition of agents which cause an increase in the level of cAMP to the medium induces an increase in Vt and Isc which is independent of the glucose. It appears to be linked to the establishment of a transepithelial transportation of $Cl^-$ (serous towards mucous) and involves a basolateral chloride transporter on the serous side and a chloride channel on the mucous side. This transportation of $Cl^-$ is associated with transportation of water in the same direction. The application, after an increase in the level cAMIP, of agents which cause an increase in the level of intracellular $Ca^{2-}$ causes a new increase in Vt and Isc associated with, without doubt, a mucous towards serous passage of $Ca^{2+}$ and a new serous towards mucous passage of $Cl^-$.

g) Measurement of the Flows of Radioactive Tracers Applied to the Study of Epithelial Cells in Culture.

This technique enables the kinetics of the exit of iodide to be monitored. The cells are cultured in 12-well plates with a dilution to 1/10 after passage. On day 3, the drugs to be tested are dissolved in medium B (37° C.) according to the required concentration. The wells are washed twice with 1 ml of medium B NaOH, 0.1% glucose, which is then replaced by 1 ml of charging solution for 30 min.

The kinetics of the exit of iodide is determined after the charging solution has been removed and the wells have been washed 3 times with 1.5 ml of medium B. For this, 1 ml of medium B is left in the well for 1 min and collected in a haemolysis tube, to be replaced by 1 ml of fresh medium B. The first minute serves as a control, and the product to be tested is added from the second minute. The operation is repeated over 10 min and the cells are then detached with 1 ml of NaOH 0.1N SDS 0.1%. The contents of each well are collected in a haemolysis tube after agitation for 25 min, and the tubes are counted for 2 min in a gamma counter.

B) Results

The study relates to molecules of the benzoquinolizinium family described above. They are tested for their ability to activate the CFTR channel. Screening of molecules as openers of the CFTR channel was carried out by measuring their effect on the efflux of radioactive iodide and on the transmembrane chloride currents (Becq et al., 1993a). These data were supplemented by measurement of the level of intracellular cyclic AMP (cAMP) and its variations in various experimental situations.

Three cell models were used to evaluate the effect of CFTR activation by benzoquiniziniums: the Xenopus ovocyte injected with the RNA which codes for CFTR (this RNA being called cRNA-CFTR in the following): the recombinant CHO cell which expresses the protein CFTR in a stable manner, and the human colon cell of the line HT29 which expresses the protein CFTR constitutively. Since the CFTR channel is mainly regulated by kinase A proteins stimulated by the level of intracellular cAMP, control experiments used derivatives of cAMP which are capable of passing through the cell membrane, and the forskoline activator of the enzyme adenylate cyclase, which leads to the synthesis of cAMP in a cell. FIG, 1 shows such an activation obtained with 500 $\mu$M c-cpt-AMP (cyclic 8-(4-chlorophenylthio)-adenosine 3',5'-monophosphate), an analogue of cAMP which passes through the membrane of cells. The activation of the CFTR channel, measured by the efflux of iodide, induces an increase in the amplitude of the efflux of iodide (expressed in % of the cell contents at time t=0), and the rate of exit of iodide (gradient of the cures at the origin).

Figure 1B:
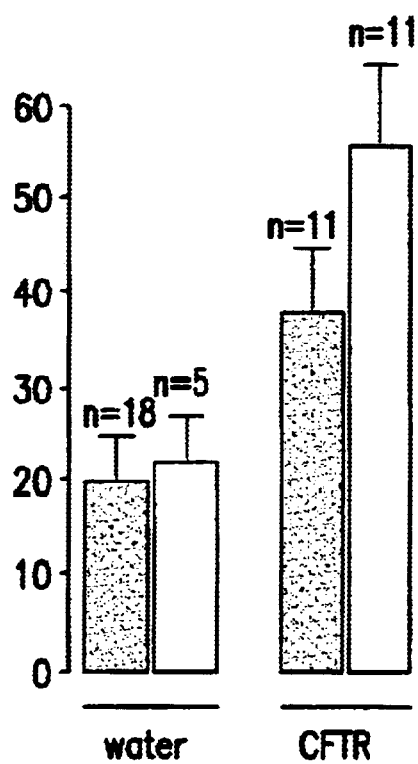

Control experiments which enable the efficacy of the molecules tested on the activity of the CFTR channel to be evaluated are the following:

1) Xenopus ovocyte: efflux of radioactive iodide and transmembrane chloride current in:

ovocytes injected with cRNA-CFTR (labelled CFTR on FIG. 1B);

the same ovocytes in the presence of activators of the cAMP route (c-ctp-AMP, forskoline);

ovocytes injected with water (labelled "water" on FIG. 1B) instead of cRNA-CFTR;

the same ovocytes in the presence of the abovementioned activators of the cAMP route.

2) CHO cell: efflux of radioactive iodide in

Figure 2A:
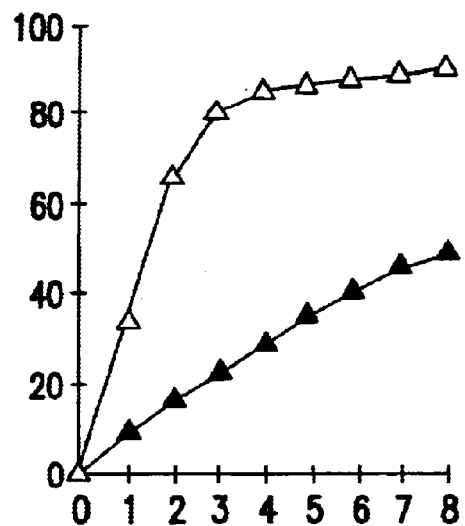
Figure 2B:
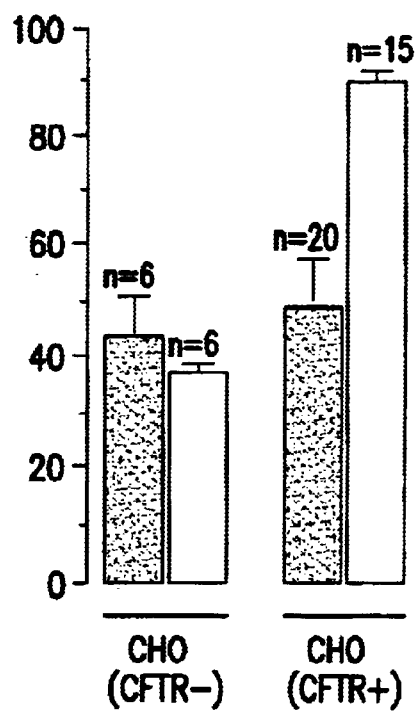

CHO cells which have not been transfected with the protein CFTR (labelled CHO-CFTR (−) on FIG. 2 B) in the presence or absence of the abovementioned activators:

CHO cells transfected with the CFTR chain (labelled CHO-CFTR (+) on FIG. 2B) in the presence or absence of the abovementioned activators.

3) HT29 cell: efflux of radioactive iodide in

HT29 cells in the absence of activator (labelled basal on FIG. 3);

cells in the presence of the abovementioned activators (labelled cAMP on FIG. 3).

The presence of a chloride channel activated by the increase in the level of intracellular calcium was tested in the presence of the calcium ionophor A23187. The effects of the activators of cAMP, A23187 and benzoquinoliziniums were evaluated under these various experimental conditions (regarded mutatis mutandis as a control, labelled basal) by their ability to promote the efflux of radioactive iodide and to increase the transmembrane chloride current.

Figure 3A:
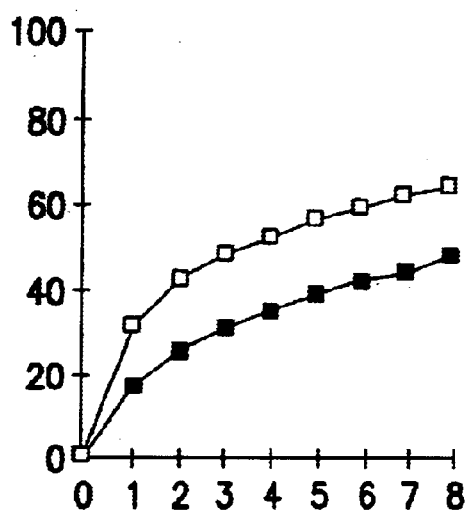

FIGS. 2A and 2B show the CFTR activation by 500 μM c-cpt-AMP in the recombinant CHO cell which expresses CFTR. In the control CHO (CFTR−) cell, c-cpt-AMP has no effect. In the HT29 cell, the CFTR channel can be stimulated by cAMP, as the increase in the amplitude of the iodide flux in the presence of 500 μM c-cpt-AMP shows (FIG. 3A and B).

Effect of Benzoquinoliziniums on the CFTR Channel Activation in the CHO Cell

Figure 4:
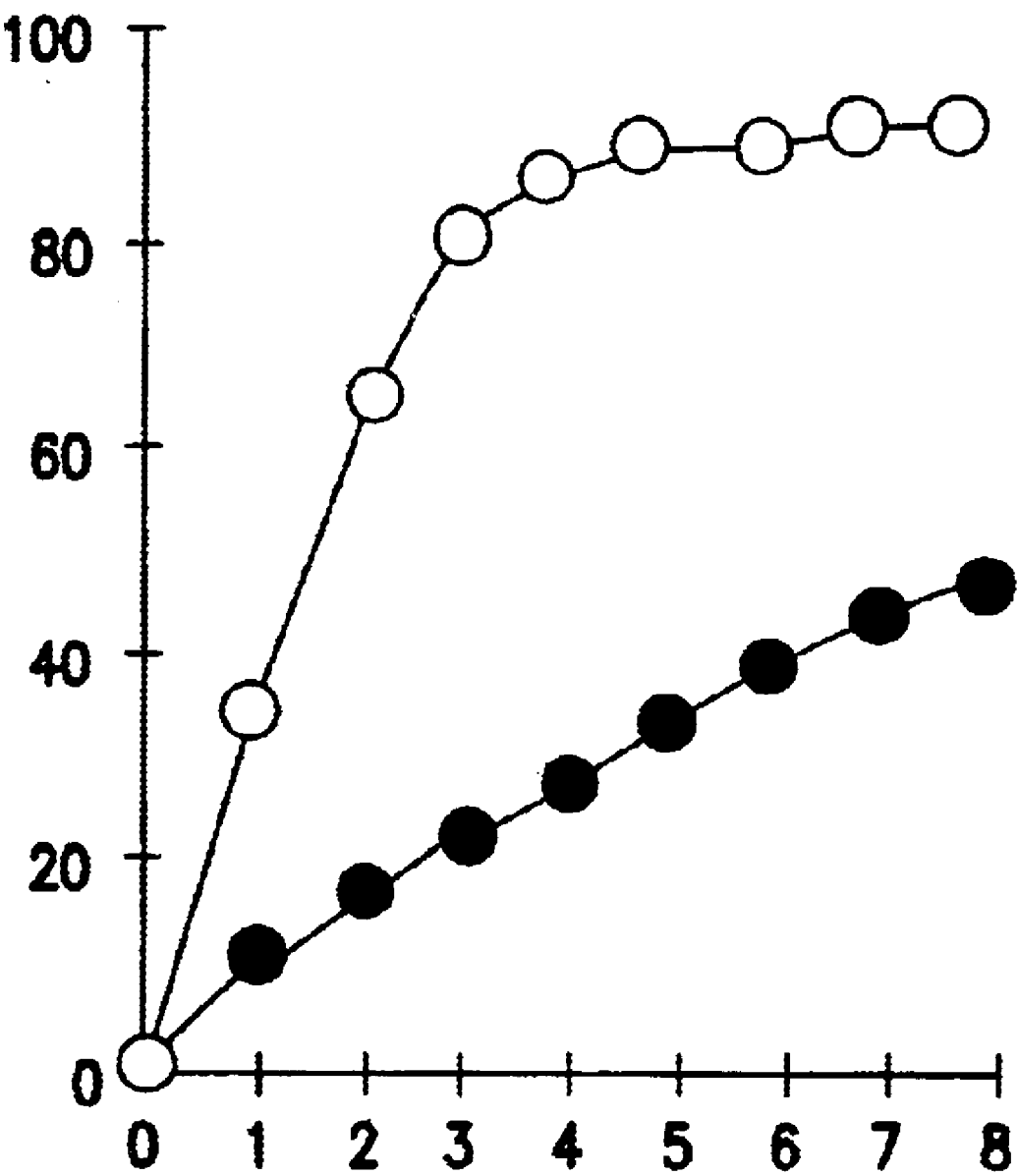
Figure 5:
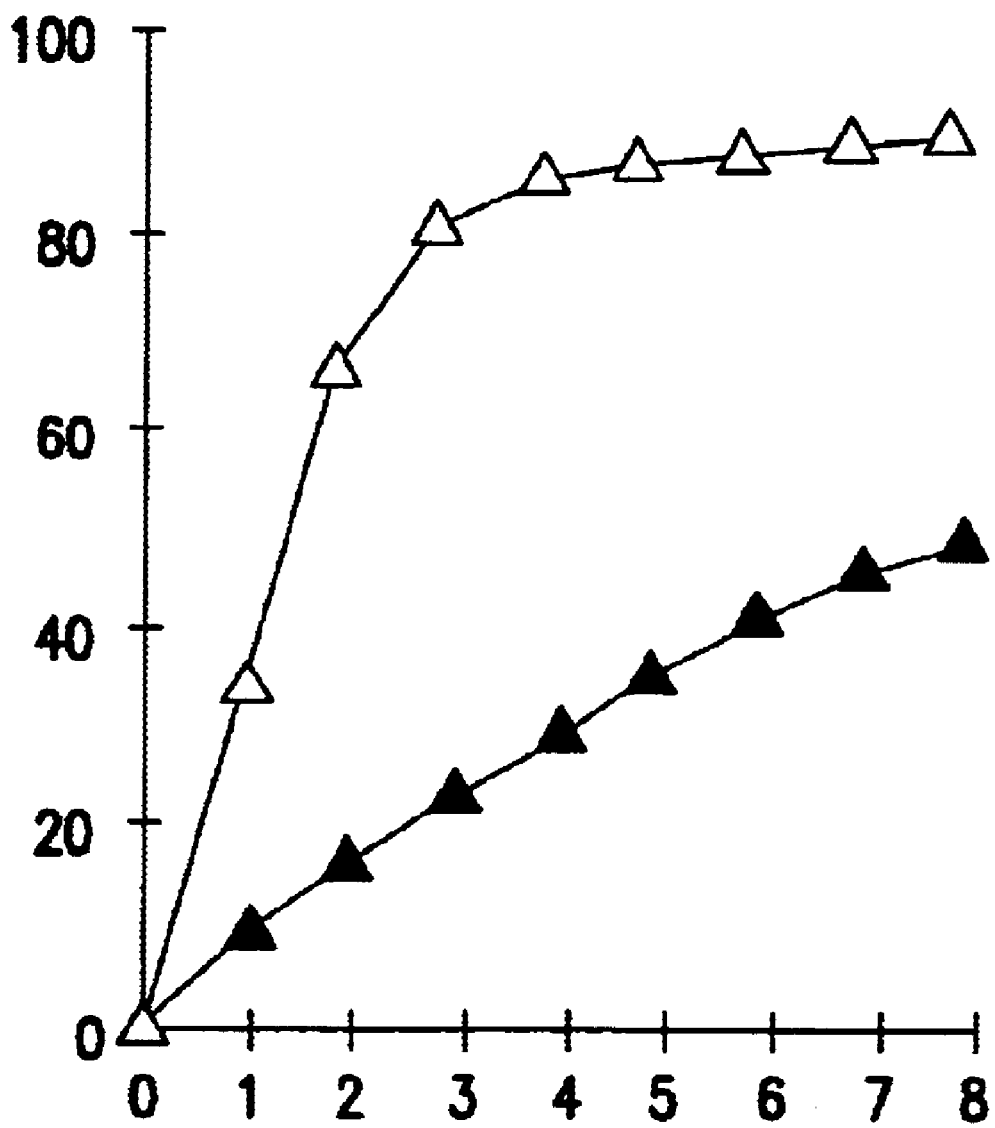
Figure 6:
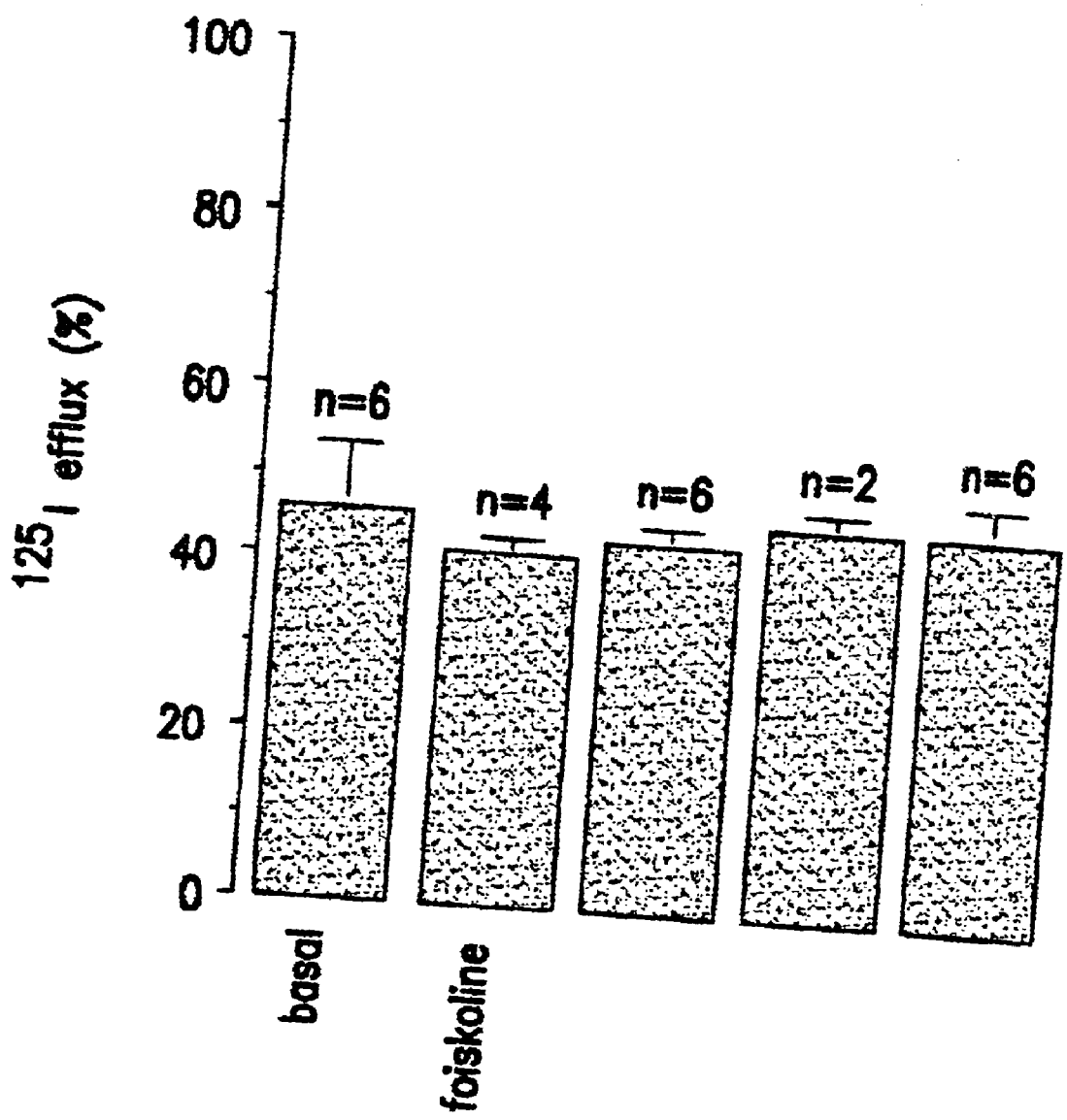
Figure 7:
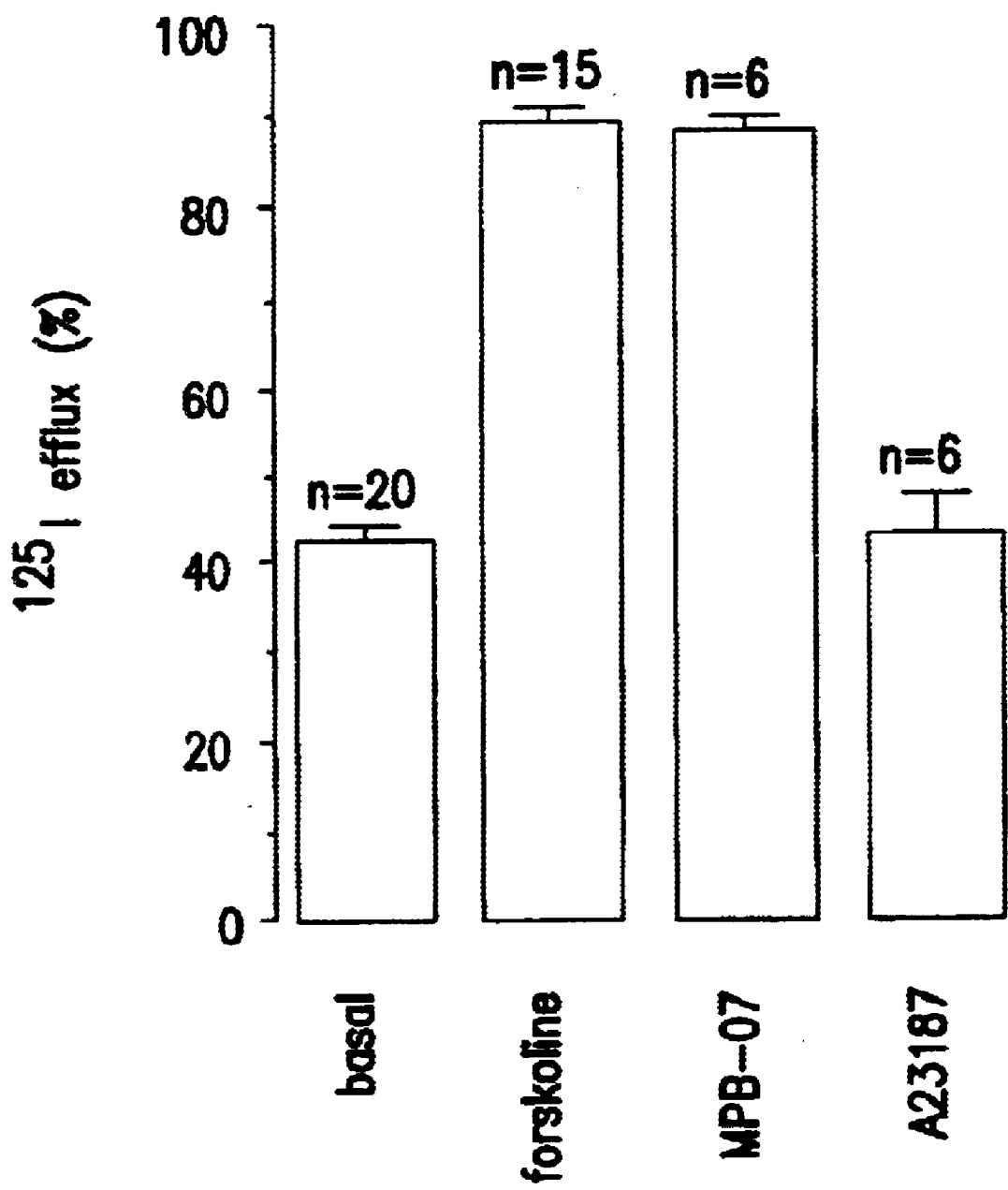

FIG. 4 shows the effect of the derivative MPB-07 (500 μM) on the efflux of iodide in the CHO (CFTR+) and CHO (CFTR−) cell. The activation of the efflux of iodide in the CHO (CFTR+) cell is comparable in intensity and rate to that induced by forskoline (5 μM), an activator of cAMP, in the CHO (CFTR+) cells (FIG. 5). The results regarding the effects of the derivative MPB-07 on the efflux of iodide in the CHO (CFTR−) and CHO (CFTR+) cells are summarized in the histograms of FIGS. 6 and 7 respectively. MPB-07 (D00 μM) also effectively stimulates the efflux of iodide which forskoline (5 μM) produces on the CHO (CFTR+) cells (FIG. 7). On these same cells. A23187 (10 μM) has no effect. In the CHO (CFTR−) cells, forskoline (5 μM). A23187 (10 μM), either separately or added together, and MPB-07 (500 μM) do not significantly modify the basal level of the efflux of iodide (FIG. 6).

Effect of Benzoquinoliziniums on CFTR Channel Activation in the HT29 Cell

The effect of MPB-07 on the efflux of iodide in the recombinant CHO cell is reproduced in the HT29 epithelial cell. The application of 500 μM c-cpt-AMP (FIG. 8A) or of 500 μM MPB-07 (FIG. 8B) triggers an efflux of iodide, with a similar rate and amplitude, which is increased with respect to the basal level (without activator) (FIG. 9).

Figure 10A:
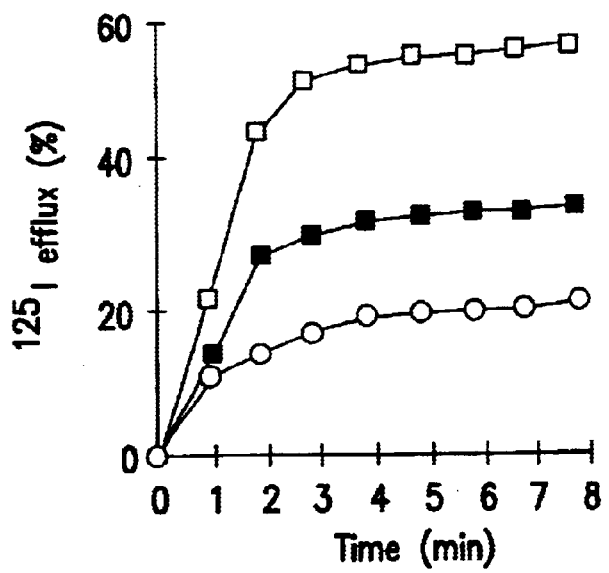

Effect of Benzoquinoliziniums on CFTR Channel Activation Expressed in the Xenopus Ovocyte MPB-07 (500 μM) stimulates the efflux of iodide in the Xenopus ovocyte. This activation (FIG. 10A) is comparable to that obtained by application of 500 μM c-cpt-AMP (FIG. 10B) and is significantly different (FIG. 11) to the efflux measured in the stimulated (cAMP and MPB-07) and non-stimulated (basal) non-injected ovocyte (FIG. 11, water) and in the ovocyte which is not stimulated but expresses CFTR (FIG. 10A, efflux labelled basal CFTR).

Structure-function Study of Benzoquinoliziniums and Correlation With the CFTR Opening The study was carried out on 16 derivatives of the benzoquinolizinium nucleus.

Tables 1 and 2 show the chemical structure of compounds of the benzoquinolizinium family tested here as a CFTR channel activator.

Tables 1 and 2 shows the results relating to the efflux measured in the presence of various compounds tested on the recombinant CHO (CFTR+) cell. The base compound, phenanthrene (table 2) does not activate the CFTR channel. Two series of molecules were tested: $NH_2$ series (table 1, MPB-26, MPB-01 to 04; table 2: MPB-24) and OH series (table 1, MPB-05 to 08, MPB-27, 29, 30 and 32; table 2: MPB-25). The percentages of CFTR channel activation are given in the corresponding tables. They show that the OH series activates CFTR with percentages of between and 110%. The $NH_2$ series is less active (10 to 30%).

In the OH series, the efficacy is the following:

MPB-05, 08, 25, 32<30<29<06<27, 07

From all the compounds studied, it seems that the presence of the OH grouping in position 6 is the determining factor as regards the ability to activate the CFTR channel:

9 compounds with OH in position 6: 45% CFTR channel activation 6 compounds with NH, in position 6: 13% CFTR channel activation.

Effect of Benzoquinoliziniums on Intracellular cAMP

Figure 12:
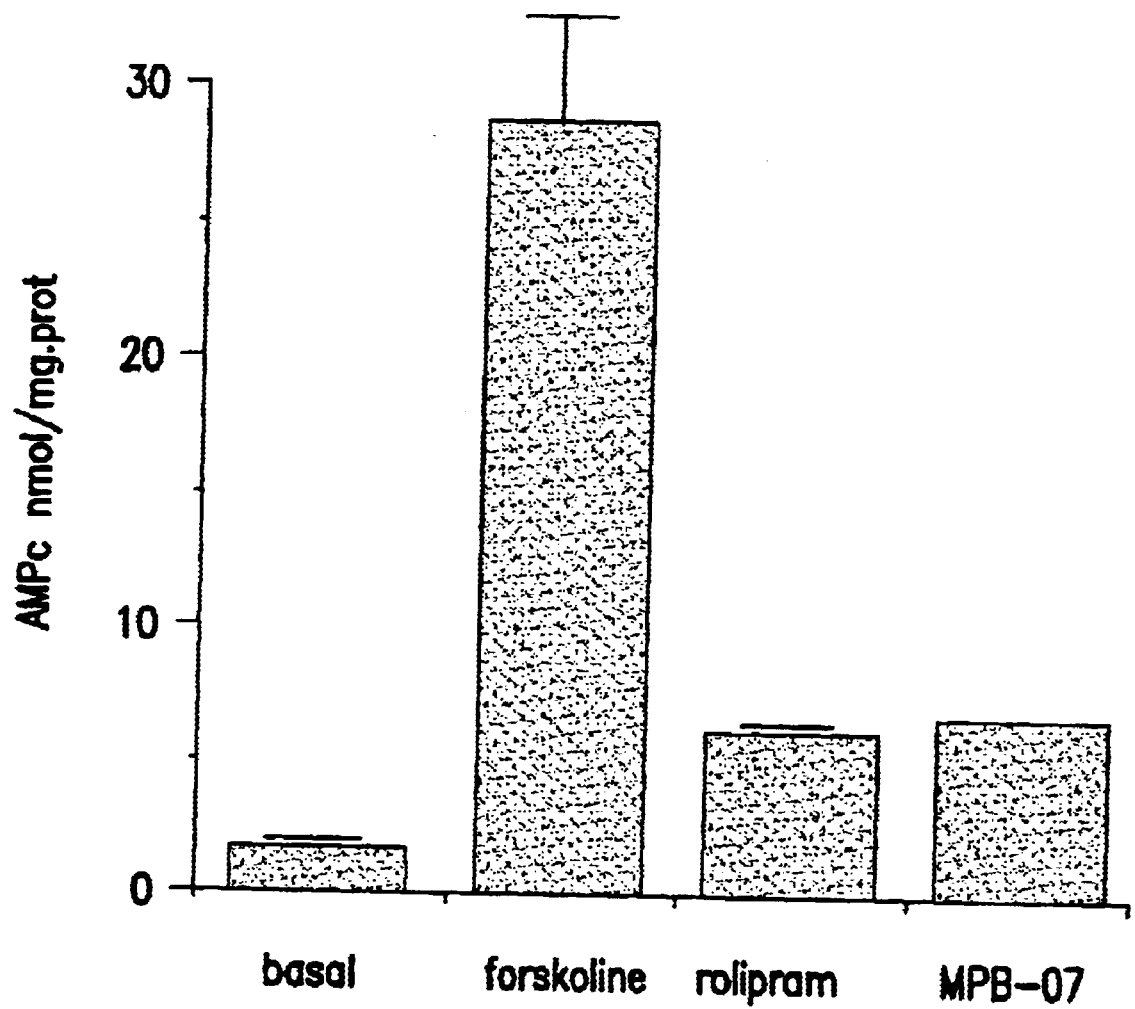

FIG. 12 shows the levels of cell cAMP in the recombinant CHO cell measured after 5 min in the presence of 5 μM forskoline (activator of the enzyme for synthesis of cAMP: adenylate cyclase), 10 μM rolipram (an inhibitor of the enzyme of cAMP degradation: type IV phosphodiesterases) and 500 μM MPB-07. The same level of cAMP is reached in the presence of the compounds MPB-07 and rolipram, but only MPB-07 triggers CFTR channel activation. The effect of forskoline on cAMP is multiplied a factor of about 4, suggesting that this effect is purely dependent on cAMP, Rolipram has no effect as a CFTR activator measured by the flow of iodide and by patch clamping. These results show that the compound MPB-07 stimulates the CFTR channel by a route independent of the cell cAMP route.

C) Conclusion

These results show that the compound MPB-07 and some members of the benzoquinolizinium family stimulate opening of the CFTR channel by a route independent of cAMP or intracellular calcium. These molecules thus represent a new family of CFTR channel activators.

Legends to Figures

FIG. 1: Effect of c-cpt-AMP on the efflux of radioactive iodide in the Xenopus ovocyte;

FIG. 1A: Curves of the efflux of $^{125}I$ (% on the ordinate) as a function of time (min on the abscissa): the curve passing through points represented by black squares corresponds to the efflux of $^{125}I$ measured as a function of time in ovocytes injected with cRNA-CFTR (curved designated basal CFTR): the curve passing through points represented by white square corresponds to the efflux of $^{125}I$ measured as a function of time in ovocytes injected with cRNA-CFTR and activated by c-cpt-AMP (curve designated CFTR+cAMP);

FIG. 1B: Histograms of the efflux of $^{125}I$ in ovocytes which have not been activated by c-cpt-AMP (shown in black) and in ovocytes activated by c-cpt-AMP (shown in white): ovocytes which have or have not been activated by c-cpt-AMP and have been injected with water are shown on the left (labelled "water"): ovocytes which have or have not been activated by c-cpt-AIMP and have been injected with cRNA-CFTR are shown on the right (labelled "CFTR"): n represents the number of experiments.

FIG. 2: Effect of c-cpt-AMP on the efflux of radioactive iodide in the CHO cells:

FIG. 2A: Curves of the efflux of $^{125}I$ (% on the ordinate) as a function of time (min on the abscise): the curve passing through points represented by black triangles corresponds to the efflux of $^{125}I$ measured as a function of time in the CHO cells which have not been activated by c-cpt-AMP (curve designated basal); the curve passing through points represented by white triangles corresponds to the efflux of $^{123}I$ measured as a function of time in the CHO cells activated by c-cpt-AMP (curve designated cAMP);

FIG. 2B: Histograms of the efflux of $^{125}I$ in the CHO cells which have not been activated by c-cpt-AMP (shown in white); the CHO cells which have or have not been activated by c-cpt-AMP and have not been transfected with the CFTR gene are shown on the left (labelled CHO (CFTR−)); the CHO cells which have or have not been activated by c-cpt-AMP and have been transfected with the CFTR gene are shown on the right (labelled CHO (CFTR+)); n represents the number of experiments.

Figure 3B:
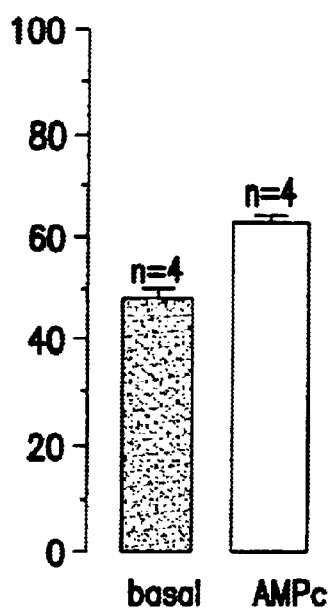

FIG. 3: Effect of c-cpt-AMP on the efflux of radioactive iodide in HT29 cells:

FIG. 3A: Curves of the efflux of $^{125}I$ (% on the ordinate) as a function of time (min on the abscise): the curve passing through points represented by black squares corresponds to the efflux of $^{125}I$ measured as a function of time in HT29 cells which have not been activated by c-cpt-AMP (curve designated basal): the curve passing through points represented by white squares corresponds to the efflux of $^{125}I$ measured as a function of time in the HT29 cells activated by c-cpt-AMP (curve designated cAMP):

FIG. 3B: Histograms of the efflux of $^{125}I$ in the HT29 cells which have not been activated b c-cpt-AMP (in black) and in the HT29 cells activated by c-cpt-AMP (in white).

FIG. 4: Effect of the derivative MPB-07 (500 μM) on the efflux of $^{125}I$ (% on the ordinate) as a function of time (min on the abscise) in the CHO cell: the curve passing through points represented by white circles corresponds to the measurement of the efflux of $^{125}I$ as a function of time in the CHO cells activated by MPB-07 and transfected with the CFTR gene (curve designated MPB-07 (CFTR+)): the curve passing through points represented by black circles corresponds to the measurement of the efflux of $^{125}I$ as a function of time in the CHO cells activated by MPB-07 but not transfected with the CFTR gene (curve designated MPB-07 (CFTR−)).

FIG. 5: Effect of "forskoline" (500 μM) on the efflux of $^{125}I$ (% on the ordinate) as a function of time (min on the abscise) in the CHO cell; the curve passing through points represented by white triangles corresponds to the measurement of the efflux of $^{125}I$ as a function time in CHO cells activated by forskoline and transfected with the CFTR gene (curve designated forskoline CHO (CFTR+)); the curve passing through points represented by black triangles corresponds to the measurement of the efflux of $^{125}I$ as a function of time in the CHO cells which have not been activated by forskoline and have been transfected with the CFTR gene (curve designated basal CHO (CFTR+)).

FIG. 6: Histograms of the efflux of 125I in the CHO cells which have not been transfected with the CFTR gene (designated CHO (CFTR−)) and:

have not been activated (basal)

have been activated by forskoline (forskoline)

have been activated by A23187 (A23187)

have been activated by A23187 and forskoline (A23187+fsk)

have been activated by MPB-07 (MPB-07)

n represents the number of experiments.

FIG. 7: Histograms of the efflux of $^{125}I$ in the CHO cells which have been transfected with the CFTR gene (designated CHO (CFTR+)) and:

have not been activated (basal)

have been activated by forskoline (forskoline)

have been activated by MPB-07 (MPB-07)

have been activated by A23187 (A23187)

n represents the number of experiments.

Figure 8A:
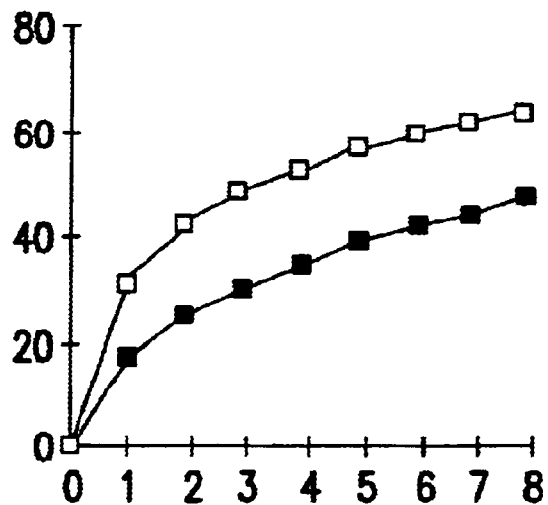
Figure 8B:
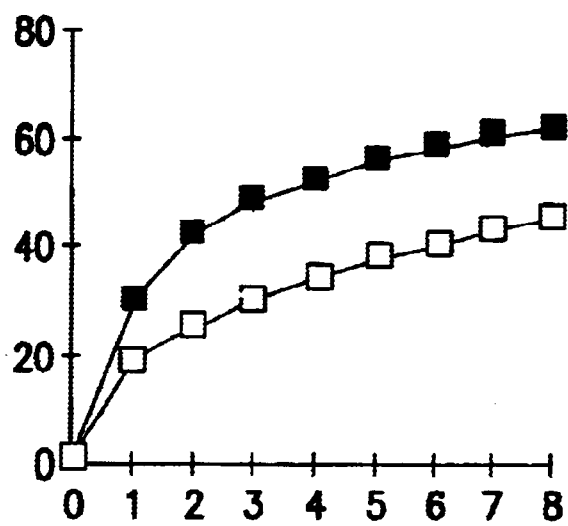
Figure 9:
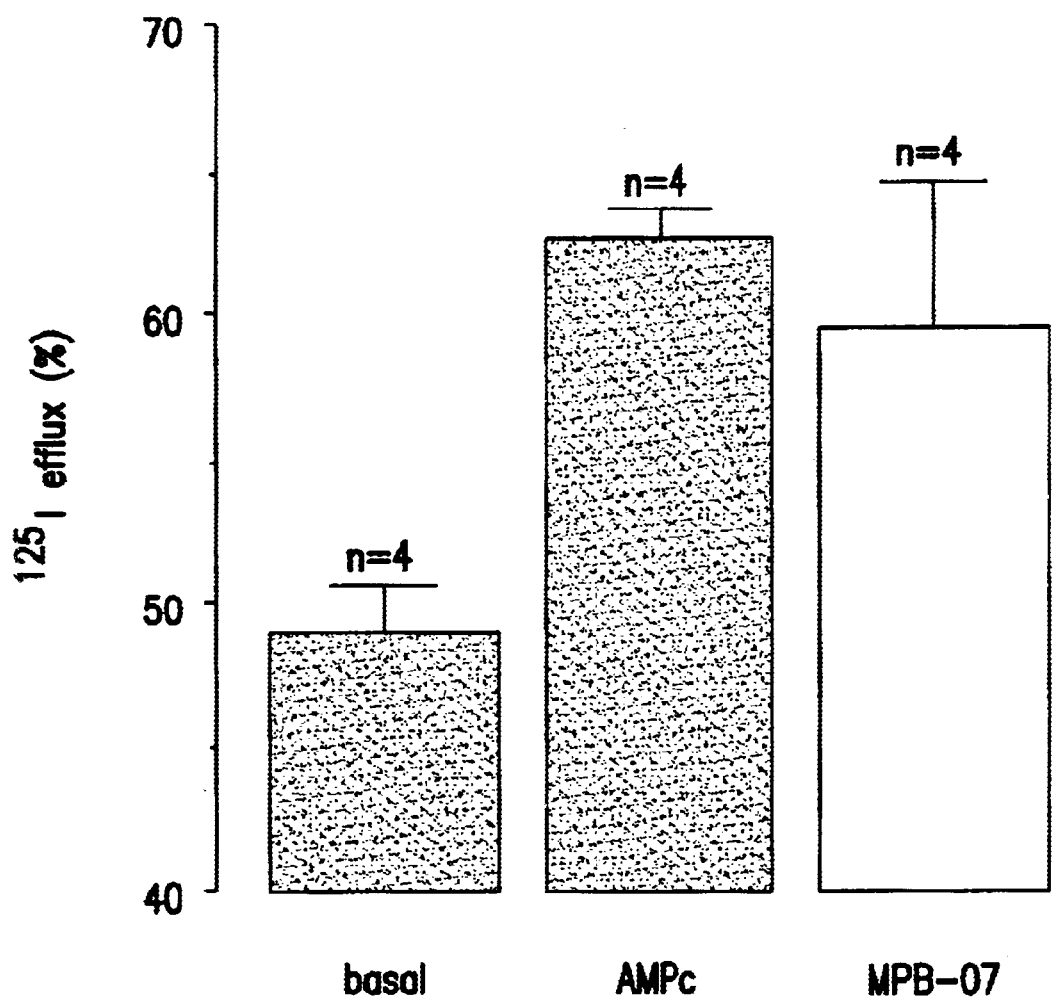

FIG. 8: Comparison of the effects of c-cpt-AMP (500 μM) and MPB-07 (500 μM) on the efflux of $^{125}I$ (% on the ordinate) as a function of time (min on the abscise) in the HT29 cells;

FIG. 8A: The curve passing through points represented by black squares corresponds to the measurement of the efflux of 125I as a function of time in the non-activated HT29 cells (curve designated basal): the curve passing through points represented by white squares corresponds to the measurement of the efflux of $^{125}I$ as a function of time in the HT29 cells activated by c-ctp-AMP (curve designated cAMP):

FIG. 8B: The curve passing through points represented by white squares corresponds to the measurement of the efflux of $^{125}I$ as a function of time in the non-activated HT29 cells (curve designated basal): the curve passing through points represented by black squares corresponds to the measurement of the efflux of $^{125}I$ as a function of time in the HT29 cells activated by MPB-07 (curve designated MPB-07).

FIG. 9: Histogram of the efflux of 125I in the HT29 cells which have not been activated (basal), have been activated by c-ctp-AMP (cAMP) and have been activated by MPB-07 (MPB-07): n represents the number of experiments.

Figure 10B:
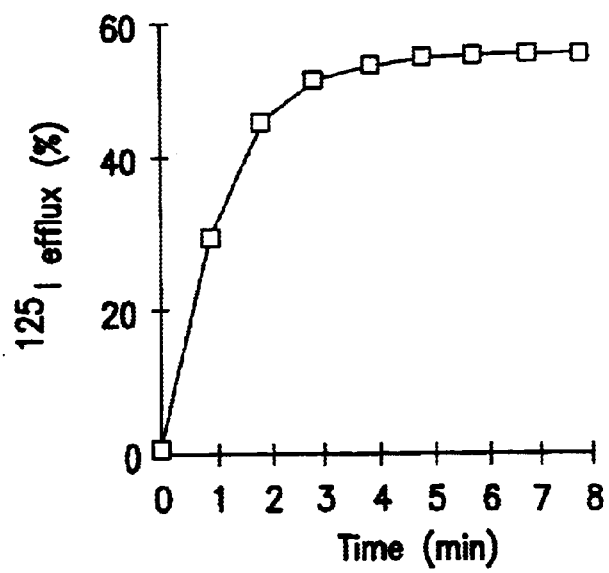

FIG. 10: Comparison of the effects of c-ctp-AMP (500 μM) on the efflux of $^{125}I$ (% on the ordinate) as a function of time (min on the abscise) in the Xenopus ovocytes;

FIG. 10A: The curve passing through points represented by white circles corresponds to the measurement of the efflux of 125I as a function of time in the ovocytes injected with water (curve designated basal water): the curve passing through points represented by black squares corresponds to the measurement of the efflux of $^{125}I$ as a function of time in the ovocytes injected with cRNA-CFTR (curve designated basal CFTR): the curve passing through points represented by white squares corresponds to the measurement of the efflux of H231 as a function of time in the ovocytes which have been injected with cRNA-CFTR and have been activated with c-ctp-AMP (curve designated CFTR+ cAMP);

FIG. 10B: The curve passing through points represented by white squares corresponds to the measurement of the efflux of 125I as a function of time in the ovocytes which have been injected with cRNA-CFTR and have activated by MPB-07 (curve designated MPB-07).

Figure 11:
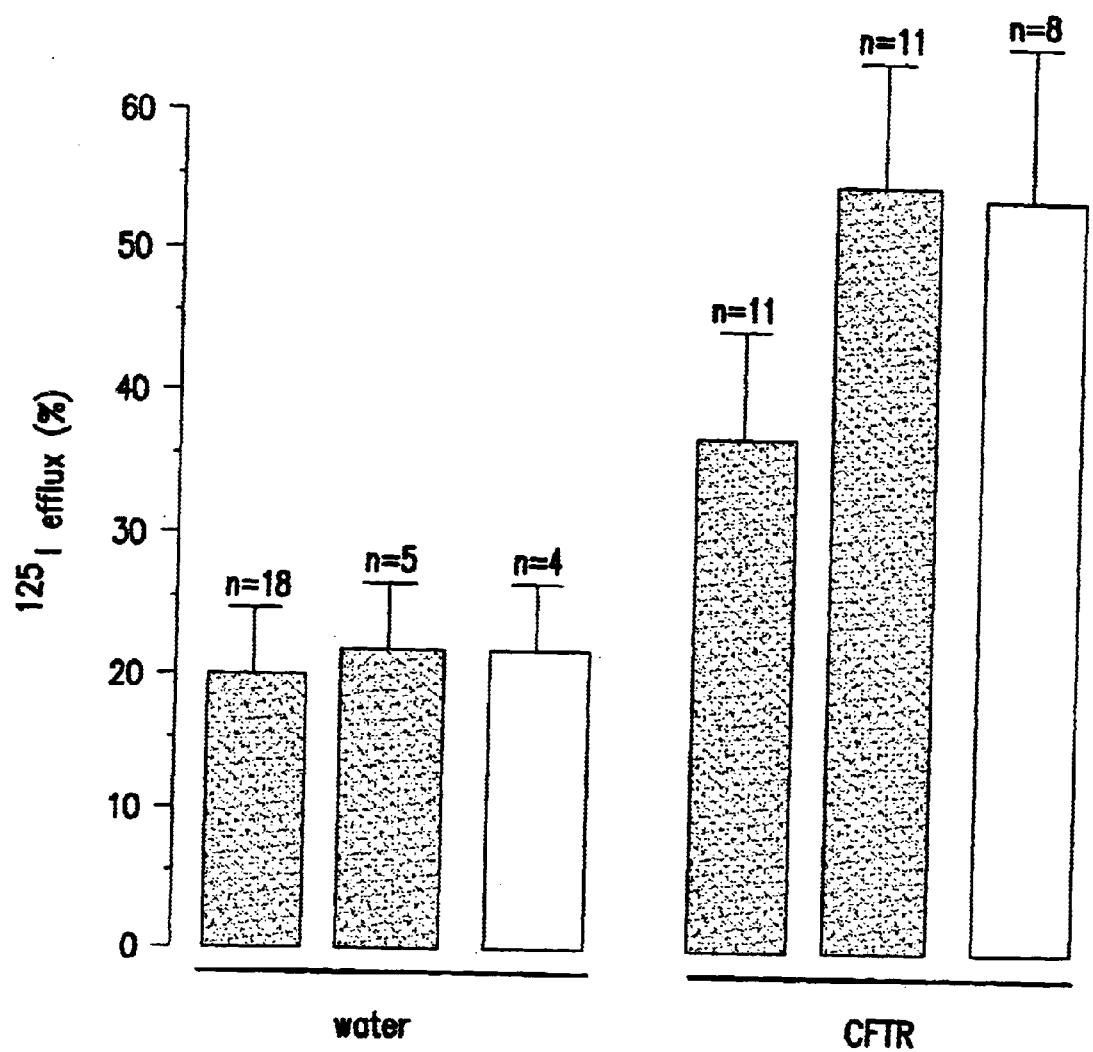

FIG. 11: Histograms of the efflux of 125I in the Xenopus ovocytes which have not been activated (basal), or have been activated by c-ctp-AMP (cAMP), or have been activated by MPB-07 (MPB-07), these ovocytes having been either injected with water (labelled "water" on the left), or injected with cRNA-CFTR (labelled "CFTR" on the right); n represents the number of experiments.

FIG. 12: Histograms representing the levels of cAMP (measured in nmol per mg of protein) in the CHO cells which have been transfected with the CFTR gene and have not been activated (basal), or have been activated by forskoline (forskoline), or have been activated by rolipram (rolipram), or have been activated by MPB-07 (MPB-07).

TABLE 1

| Compound | X | Y | R | % activation relative to control |
|---|---|---|---|---|
| MPB-26 | Cl | NH$_2$ | H | 30 |
| MPB-03 | Cl | NH$_2$ | 9-Cl | 18 |
| MPB-04 | Cl | NH$_2$ | 7Cl | 11 |
| MPB-06 | Br | OH | H | 53 |
| MPB-05 | Cl | OH | H | 20 |
| MPB-07 | Cl | OH | 10-Cl | 110 |
| MPB-08 | Cl | OH | 9-Cl | 22 |
| MPB-27 | Cl | OH | 7-Cl | 95 |
| MPB-30 | Cl | OH | 8-Cl | 28 |
| MPB-29 | Cl | OH | 9-F | 42 |
| MPB-32 | Cl | OH | 8-Br | 13 |
| control (basal) | | | | 0 |
| forskoline | | | | 109 |

N.B.: forskoline: 5 µM, MPB et phenanthrene 500 µM.

TABLE 2

| Compound | X | Y | R | % activation relative to control |
|---|---|---|---|---|
| phenanthrene | H | H | H | <5 |
| MPB-24 | H | NH$_2$ | H | 18 |
| MPB-25 | H | OH | H | 25 |

BIBLIOGRAPHY

Becq F. et al. (1993a). FEBS Lett, 327: 337–342
Becq F. et al. (1993b). Pflügers Arch 425: 1–8
Becq F. et al. (1994). PNAS 91. 9160–9164
Chang X-B et al. (1993). J. Biol Chem, 268: 11304–11311
Cutting G. R. et al. (1990). Nature 346: 366–369
Dalemans W. et al. (1991). Nature 354: 526–528
Dils F. (1979). J. Int. Med, Res 7: 302–304
Drumm M. L. et al. (1991). Science 254: 1797–1999
Gregor R. J. et al. (1994). Mol. Cell. Biol, 11: 3886–3893
Grem J. L. (1990). Cancer cells, 2: 131–137
Gribkoff V. K. et al. (1994). J. Biol. Chem, 269: 10983–10986
Hamill O. P. et al. (1981). Pflügers Arch 391: 85–100
Kerem B-S. et al. (1989). Science 245: 1073–1080
Olesen S. P. et al. (1994). Europ. J. Pharm, 251: 53–59
Riordan J. R. et al. (1989). Science 245: 1066–1072
Sheppard D.N, et al. (1993). Nature 362: 160–164
Tabcharani J. A. et al. (1991). Nature 352: 628–631
Tsui L-C & Buchwald M. (1991). Advances in human genetic 20: 153–266
Van Eygen M. et al. (1976). The Lancet 1: 382–385

What is claimed is:

1. Compositions for activating cystic fibrosis transmembrane conductance regulator channels in vivo, said compositions containing at least one benzo[c]quinolizinium derivative selected from the group consisting of:

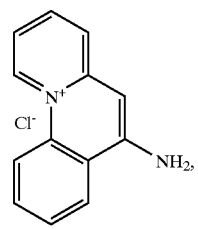
(compound 11 or MPB-26)

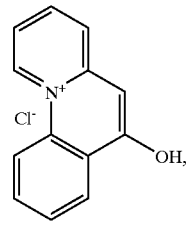
(compound 12 or MPB-05)

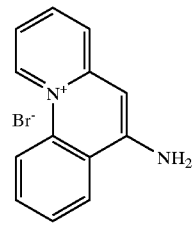
(compound 13 or MPB-01)

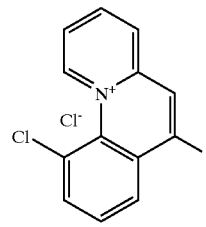
(compound 14 or MPB-02)

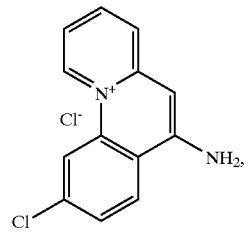
(compound 15 or MPB-03)

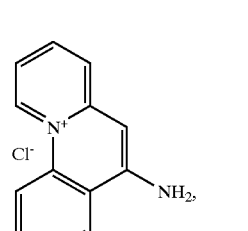
(compound 16)

(compound 17)
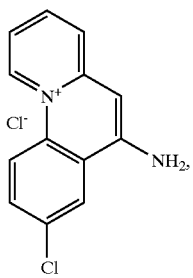
(compound 18 or MPB-06)
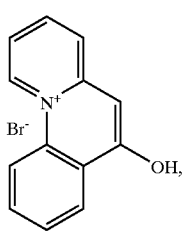
(compound 19 or MPB-07)
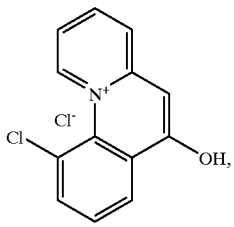
(compound 20 or MPB-08)
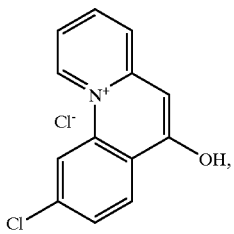
(compound 21 or MPB-27)
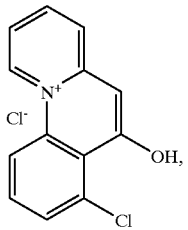
(compound 22)
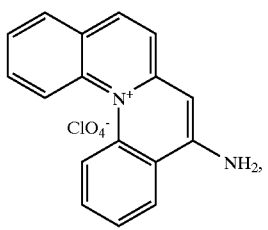
(compound 23)
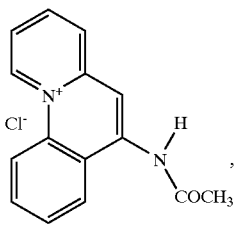
(compound 24)
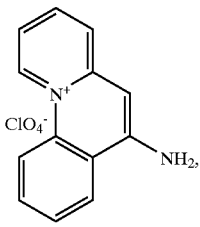
(compound 25 or MPB-30)
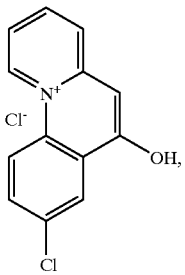
(compound 26 or MPB-29)
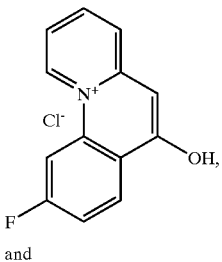
and
(compound 27 or MPB-32)
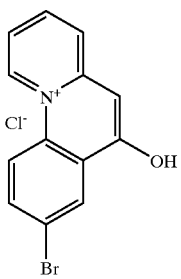
in combination with a physiologically acceptable vehicle.
* * * * *